US010952592B2

(12) United States Patent
Saito

(10) Patent No.: US 10,952,592 B2
(45) Date of Patent: Mar. 23, 2021

(54) OPTICAL SYSTEM HAVING VOICE COIL MOTOR FOR MOVING A LENS AND SENSOR FOR DETECTING POSITION OF LENS AND ENDOSCOPE SYSTEM HAVING THE OPTICAL SYSTEM

(71) Applicant: OLYMPUS CORPORATION, Tokyo (JP)

(72) Inventor: Kanako Saito, Mitaka (JP)

(73) Assignee: OLYMPUS CORPORATION, Tokyo (JP)

( * ) Notice: Subject to any disclaimer, the term of this patent is extended or adjusted under 35 U.S.C. 154(b) by 368 days.

(21) Appl. No.: 15/960,627

(22) Filed: Apr. 24, 2018

(65) Prior Publication Data

US 2018/0235436 A1    Aug. 23, 2018

Related U.S. Application Data

(63) Continuation of application No. PCT/JP2015/080626, filed on Oct. 29, 2015.

(51) Int. Cl.
*A61B 1/05* (2006.01)
*H04N 5/225* (2006.01)
*A61B 1/00* (2006.01)
*A61B 1/04* (2006.01)

(52) U.S. Cl.
CPC ........ *A61B 1/00006* (2013.01); *A61B 1/0019* (2013.01); *A61B 1/00057* (2013.01);
(Continued)

(58) Field of Classification Search
CPC ............ A61B 1/00006; A61B 1/00057; A61B 1/00096; A61B 1/00133; A61B 1/00188;
(Continued)

(56) References Cited

U.S. PATENT DOCUMENTS

2012/0150471 A1    6/2012 Muto
2013/0128098 A1    5/2013 Hamamura
(Continued)

FOREIGN PATENT DOCUMENTS

JP    S54-094028 A    7/1979
JP    H04-331907 A    11/1992
(Continued)

OTHER PUBLICATIONS

International Search Report dated Jan. 26, 2016 issued in PCT/JP2015/080626.

*Primary Examiner* — John P Leubecker
(74) *Attorney, Agent, or Firm* — Scully, Scott, Murphy & Presser, P.C.

(57) ABSTRACT

An optical system includes: a first optical element; a first movable frame; a holding frame; a voice coil motor; a first position detection unit configured to detect information related to a position of the first movable frame with respect to the holding frame and generate a first position signal; a determination unit configured to determine whether the first position signal is normal; and a drive control unit configured to perform, when the determination unit determines that the first position signal is normal, first drive control for driving the first movable frame by controlling, based on the first position signal, a current allowed to flow in the coil or configured to perform, when the determination unit determines that the first position signal is not normal, second drive control for driving the first movable frame by flowing a current with a predetermined value in the coil.

10 Claims, 12 Drawing Sheets

(52) U.S. Cl.
CPC ...... *A61B 1/00096* (2013.01); *A61B 1/00133* (2013.01); *A61B 1/00188* (2013.01); *A61B 1/04* (2013.01); *A61B 1/05* (2013.01); *H04N 5/2253* (2013.01); *H04N 5/2254* (2013.01)

(58) Field of Classification Search
CPC ........... A61B 1/04; A61B 1/05; A61B 1/0661; A61B 1/0019; G02B 23/2438; H04N 5/2254; H04N 5/2253
See application file for complete search history.

(56) References Cited

U.S. PATENT DOCUMENTS

| | | | |
|---|---|---|---|
| 2013/0217965 A1* | 8/2013 | Sasamoto | A61B 1/018 600/109 |
| 2014/0039257 A1* | 2/2014 | Higuchi | A61B 1/00006 600/109 |
| 2014/0111628 A1* | 4/2014 | Yoshino | G03B 13/36 348/65 |
| 2014/0379103 A1* | 12/2014 | Ishikawa | G05B 15/02 700/56 |
| 2015/0256778 A1* | 9/2015 | Kusaka | G02B 7/34 348/302 |
| 2016/0037079 A1 | 2/2016 | Gocho et al. | |
| 2016/0282601 A1* | 9/2016 | Kono | A61B 1/00188 |

FOREIGN PATENT DOCUMENTS

| | | |
|---|---|---|
| JP | 2011-138007 A | 7/2011 |
| JP | 2013-109107 A | 6/2013 |
| JP | 5384320 B2 | 1/2014 |
| WO | WO 2015/015877 A1 | 2/2015 |

\* cited by examiner

OPTICAL SYSTEM HAVING VOICE COIL MOTOR FOR MOVING A LENS AND SENSOR FOR DETECTING POSITION OF LENS AND ENDOSCOPE SYSTEM HAVING THE OPTICAL SYSTEM

CROSS-REFERENCE TO RELATED APPLICATION

This application is a continuation of International Application No. PCT/JP2015/080626, filed on Oct. 29, 2015, the entire contents of which are incorporated herein by reference.

BACKGROUND

The present disclosure relates to an optical system and an endoscope system.

An endoscope system in which an endoscope is introduced into a living body and a diagnosis of the living body is carried out by observing an image of an object captured by the endoscope has been widely used. In the endoscope system, a deep depth of field is needed in order to avoid an obstacle to diagnosis and treatment performed by a physician, such as a doctor or a nurse. In recent years, because the depth of field is decreased due to high pixelation of an image sensor, there is a proposed endoscope system in which autofocus (hereinafter, also referred to as autofocus (AF)) is performed, thereby focusing on the object. As an actuator used to perform autofocus, voice coil motors (VCM) are usually used.

As a typical problem of endoscopes, even if a driving unit that performs AF is out of control during treatment, there is a need to maintain the resolution enough to continue the treatment without pulling out the endoscope from the subject. For example, because a position detection device that detects the position of a moving lens is electrically weak and may possibly be failed due to temperature, humidity, or the like, a countermeasure against a failure of the position detection device is needed. As a technique of performing such a countermeasure, there is a proposed technique that includes an absolute position detection sensor that detects an absolute value of the position of a moving lens and a relative position detection sensor that detects an amount of displacement of the moving lens; that detects, by using a detection result of each sensor, whether abnormality is present in the relative position detection sensor; and that determines, if abnormality is present in the relative position detection sensor, the position of the moving lens based on the detection results obtained from the absolute position detection sensor (for example, see Japanese Patent No. 5384320).

SUMMARY

An optical system according to one aspect of the present disclosure includes: a first optical element configured to transmit light; a first movable frame configured to hold the optical element and move along a predetermined direction; a holding frame configured to hold the first movable frame; a voice coil motor including a magnet and a coil and configured to move the first movable frame relative to the holding frame along the predetermined direction; a first position detection unit configured to detect information related to a position of the first movable frame with respect to the holding frame and generate a first position signal; a determination unit configured to determine, based on the first position signal detected by the first position detection unit, whether the first position signal is normal; and a drive control unit configured to perform, when the determination unit determines that the first position signal is normal, first drive control for driving the first movable frame by controlling, based on the first position signal, a current allowed to flow in the coil or configured to perform, when the determination unit determines that the first position signal is not normal, second drive control for driving the first movable frame by flowing a current with a predetermined value in the coil.

The above and other features, advantages and technical and industrial significance of this disclosure will be better understood by reading the following detailed description of presently preferred embodiments of the disclosure, when considered in connection with the accompanying drawings.

DETAILED DESCRIPTION

In the following, modes for carrying out the present disclosure (hereinafter, referred to as an "embodiment") will be described.

First Embodiment

Figure 1:
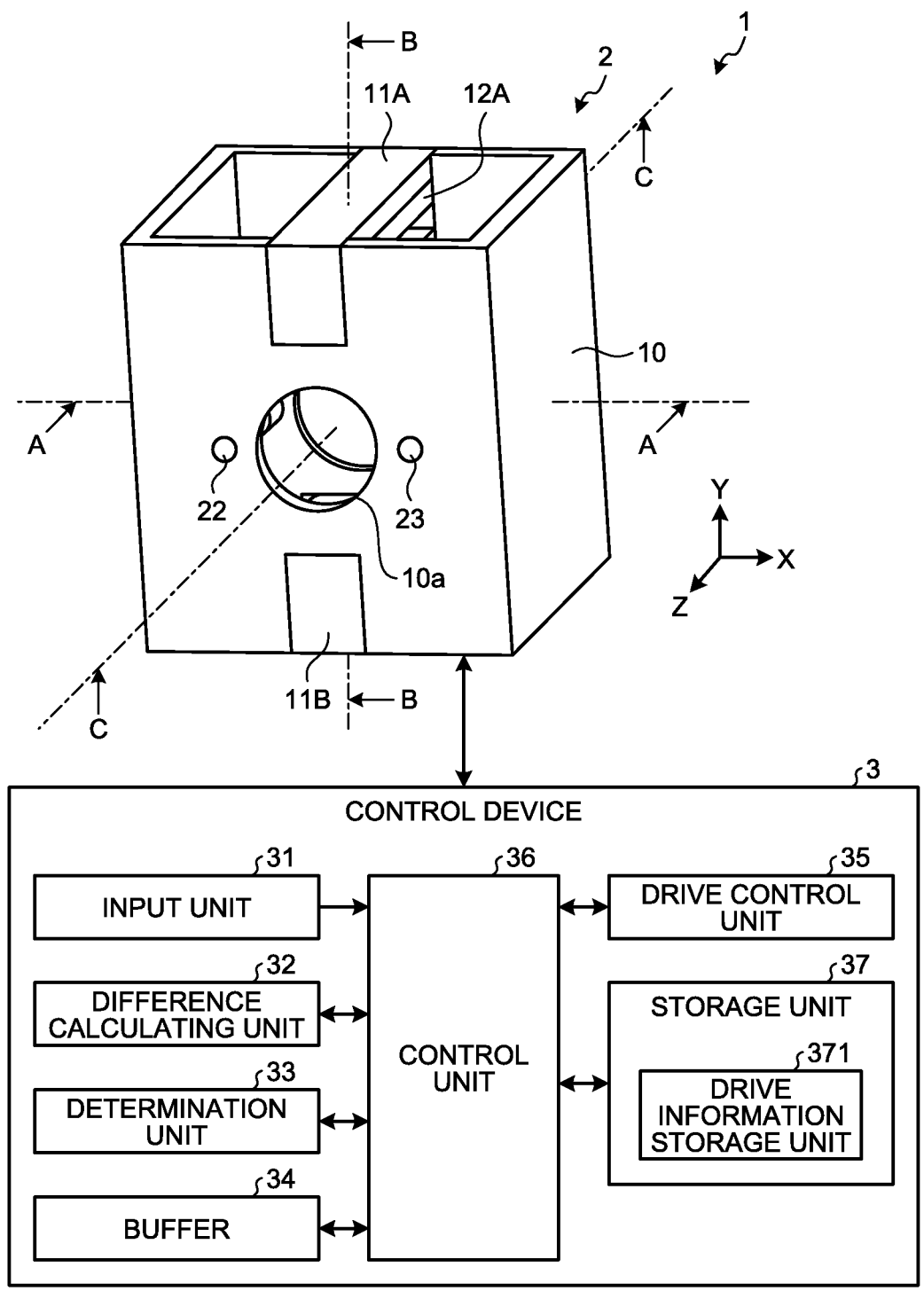
FIG. 1 is a schematic view illustrating, in outline, the configuration of an optical system according to a first embodiment.
Figure 2:
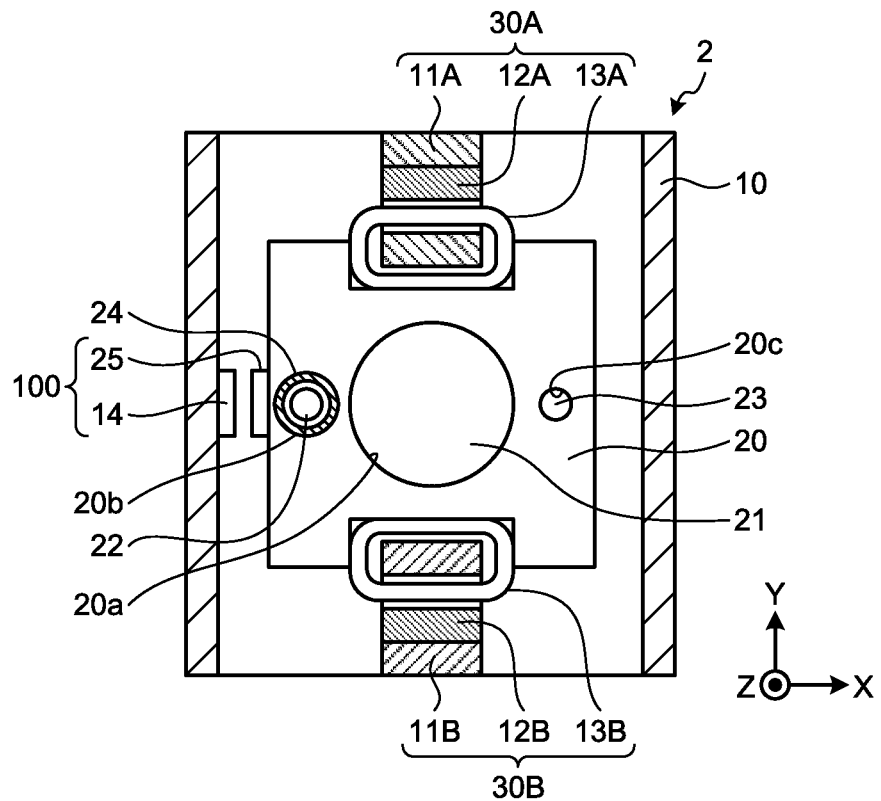
FIG. 2 is a sectional view taken along line A-A in FIG. 1.
Figure 3:
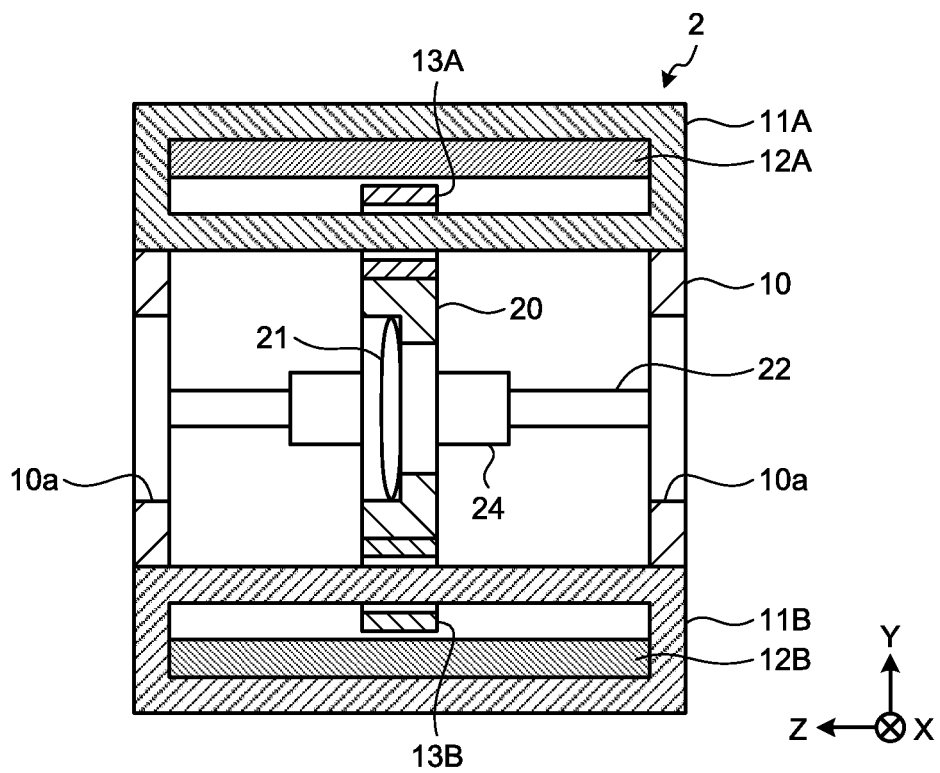
FIG. 3 is a sectional view taken along line B-B in FIG. 1.
Figure 4:
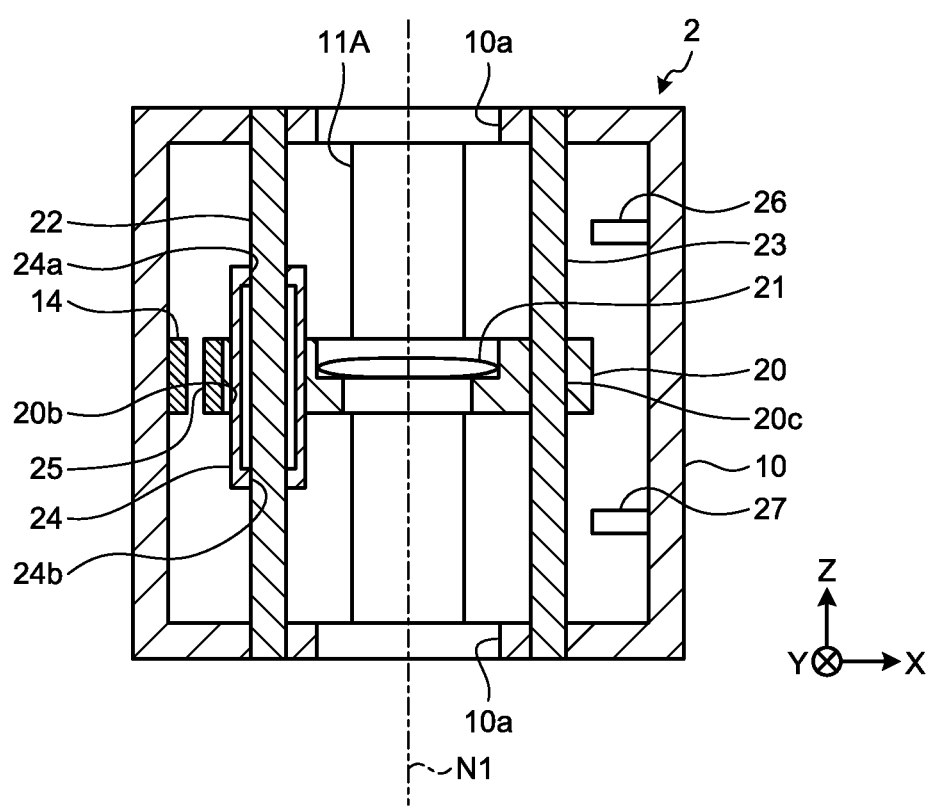
FIG. 4 is a sectional view taken along line C-C in FIG. 1.

FIG. 1 is a schematic view illustrating, in outline, the configuration of an optical system according to a first embodiment. FIG. 2 is a sectional view taken along line A-A in FIG. 1 and is a sectional view of the plane, as the cutting plane, parallel to the XY plane of the orthogonal coordinate system illustrated in FIG. 1. FIG. 3 is a sectional view taken along line B-B in FIG. 1 and is a sectional view of the plane, as the cutting plane, parallel to the YZ plane of the orthogonal coordinate system illustrated in FIG. 1. FIG. 4 is a sectional view taken along line C-C in FIG. 1 and is a sectional view of the plane, as the cutting plane, parallel to the XZ plane of the orthogonal coordinate system illustrated in FIG. 1. A description will be given with the assumption that, in the sectional view illustrated in FIGS. 2 to 4, the cutting plane passes through the center of a moving lens 21, which will be described later.

An optical system 1 illustrated in FIG. 1 includes an optical unit 2 that may move a lens in an optical axis direction and a control device 3 that performs drive control of each of components including the optical unit 2 and that performs input/output control of information with respect to each of the components.

The optical unit 2 includes a fixed frame 10 (holding frame) that is fixed to a casing of an imaging device or a distal end portion of the endoscope; a movable frame 20 that may move with respect to the fixed frame 10; the moving lens 21 provided on the movable frame 20; a main shaft 22 that supports the movable frame 20 and that guides the movement direction of the movable frame 20 with respect to the fixed frame 10; a secondary shaft 23 that supports the movable frame 20 and that guides the movement direction of the movable frame 20 with respect to the fixed frame 10; a bearing 24 that is fixed to the movable frame 20 and that is in contact with the main shaft 22 in a freely slidable manner; stoppers 26 and 27 that are provided at both ends of the movement direction of the movable frame 20 and that regulate a movement of the movable frame 20; voice coil motors 30A and 30B that generate a driving force for moving the movable frame 20 with respect to the fixed frame 10; and a position detection unit 100 that detects the position of the movable frame 20 with respect to the fixed frame 10.

The fixed frame 10 has a hollow prism shape in which hollow space having a prism shape is formed. On the fixed frame 10, a through hole 10a extending in the direction orthogonal to the central axis of the hollow prism shape in the direction through which the hollow prism shape extends (in the first embodiment, the Z-axis direction illustrated in FIG. 1) is formed. Furthermore, on one end of the opening direction of the fixed frame 10 (in the first embodiment, the Y-axis direction illustrated in FIG. 1), a yoke 11A, which will be described later, is provided, whereas, on the other end of the opening direction, a yoke 11B, which will be described later, is provided. The yokes 11A and 11B each have a ring shape formed by using a material having a high magnetic permeability, such as iron.

On the movable frame 20, a holding hole 20a that holds the moving lens 21, an insertion hole 20b through which the bearing 24 is inserted and that supports the bearing 24, and an insertion hole 20c through which the secondary shaft 23 is inserted and that supports the secondary shaft 23 are formed. The movable frame 20 holds the moving lens 21 such that the optical axis of the moving lens 21 that is, for example, an axis N1 illustrated in FIG. 4 and that is the optical axis extending along the Z-axis direction substantially matches the central axis of the through hole 10a. The insertion hole 20b is a hole having a diameter in accordance with the diameter of the outer circumference of the bearing 24. The insertion hole 20c is a hole having a diameter in accordance with the diameter of the outer circumference of the secondary shaft 23. The movable frame 20 is preferably formed by using, from the viewpoint of heat resistance, a light metal or a heat-resistant resin. The light metal may be a metal, such as aluminum, magnesium, titanium, and beryllium, or may be an alloy including these metals. The heat-resistant resin may be, for example, a resin having a heat resistant temperature of 60° C. or higher. The moving lens 21 is formed by using one or a plurality of lenses.

The main shaft 22 has a rod shape extending in the Z-axis direction and both ends of the main shaft 22 are fixed to the fixed frame 10. The main shaft 22 is preferably formed by using, from the viewpoint of heat resistance, a metal material or an alloy.

The secondary shaft 23 has a rod shape extending in the Z-axis direction and both ends of the secondary shaft 23 are fixed to the fixed frame 10. The secondary shaft 23 is disposed on the opposite side of the main shaft 22 with respect to the central axis of the moving lens 21. The secondary shaft 23 is preferably formed by using, from the viewpoint of heat resistance, a metal material or an alloy.

The bearing 24 has a cylindrical shape extending in the Z-axis direction, covers a part of the outer circumference of the main shaft 22, and is held by the movable frame 20. The bearing 24 has sliding units 24a and 24b that are disposed at both ends of the bearing 24 and that is placed in contact with the main shaft 22 in a freely slidable manner. The bearing 24 is preferably formed by using, from the viewpoint of heat resistance, a metal material, alloy, or heat-resistant resin.

A lubricant is applied to the outer circumference of the main shaft 22 or the contact portion (end portion) of the main shaft 22 of the bearing 24. The lubricant may be grease or lubricating oil. Furthermore, as a lubricating means, a solid lubricant may be provided, fluorine lubrication plating, a coating process using lubricating alumite may be used. The lubricating means preferably has a heat resistant temperature of, for example, 60° C. or higher and any means may be used as long as the lubricating effect may be obtained.

The stoppers 26 and 27 are provided at the both ends of the movement direction of the movable frame 20 and regulate the movement of the movable frame 20. In the first embodiment, a description will be given with the assumption that the stopper 26 regulates the movement of the movable frame 20 toward the image sensor side (on the side in which the focal point moves to a far point) and the stopper 27 regulates the movement of the movable frame 20 toward the object side (on the side in which the focal point moves to a near point).

The voice coil motor 30A includes the yoke 11A, a magnet 12A that is attached to the inner circumferential side of the yoke 11A, and a coil 13A that is supported by the movable frame 20 and that is wound around the yoke 11A on the opposite side of the side on which the magnet 12A is attached. The magnet 12A is implemented by using a permanent magnet and has a shape extending in the Z-axis direction.

The voice coil motor 30B is supported by the yoke 11B, the magnet 12B that is attached to the inner circumferential side of the yoke 11B, and a coil 13B that is supported by the movable frame 20 and that is wound around the yoke 11B on the opposite side of the side on which the magnet 12B is attached. The magnet 12B is implemented by using a permanent magnet and has a shape extending in the Z-axis direction.

In this case, the magnetic polarization direction of the magnets 12A and 12B is the Y-axis direction that is orthogonal to the optical axis direction (Z-axis direction) of the moving lens 21. Furthermore, more commonly, the magnetic polarization direction of the magnets 12A and 12B may be the direction intersecting the direction of the optical axis (Z-axis).

When a current is allowed to flow in the coils 13A and 13B, due to the effect of the magnetic field of the magnets 12A and 12B, a force in the Z-axis direction is generated in the movable frame 20 and thus the movable frame 20 moves in the Z-axis direction with respect to the fixed frame 10. For example, by controlling the current allowed to flow in each of the coils 13A and 13B, it is possible to move the movable frame 20 in a desired direction parallel to the main shaft 22.

The position detection unit 100 is attached to the fixed frame 10 and is formed by a single hall effect sensor 14 that is a position detection sensor and a detection-purpose magnet 25 that is provided at the movable frame 20. The hall effect sensor 14 detects the magnetic field strength at predetermined time intervals, sequentially converts the detected magnetic field strength to a voltage value, and outputs the voltage value as a position signal to the control device 3. The hall effect sensor 14 detects, for example, a magnetic field in the direction orthogonal to the longitudinal direction of the main shaft 22 (the movement direction of the movable frame 20). The detection-purpose magnet 25 is disposed on the side surface that is in the vicinity of the main shaft 22 and that is in the direction orthogonal to the optical axis of the movable frame 20. Furthermore, the detection-purpose magnet 25 is preferably disposed at the position in which the straight line that passes the center and that extends in the X-axis direction intersects the central axis of each of the main shaft 22 and the secondary shaft 23.

In the following, the configuration of the control device 3 will be described. The control device 3 includes an input unit 31, a difference calculating unit 32, a determination unit 33, a buffer 34, a drive control unit 35, a control unit 36, and a storage unit 37.

The input unit 31 is an interface for receiving an input to the control device 3 received from a user or the like and is formed by including a power supply switch for turning on/off of a power supply, an indication input button for indicating the target position or the movement direction of the movable frame 20, and the like. Furthermore, if a focus operation is manually performed, an indication signal (indication value) related to focusing (movement of the movable frame 20) is input via the input unit 31 and, in a case of automatic focus, a focus operation is performed under the control of the control unit 36. In the indication value, a numerical value that is attached in the moving range of, for example, the movable frame 20 and that indicates the position of the movable frame 20 in the moving range is included.

The difference calculating unit 32 calculates a difference between the current position of the movable frame 20 and, in a case of manual focus, an indication input that has been input via the input unit 31 or, in a case of automatic focus, the position indicated by the indication input that has been input from the control unit 36. This difference is a value indicating a movement amount and the movement direction of the movable frame 20. The movement direction is obtained by determining, based on plus and minus of the difference between the current position (signal value) of the movable frame 20 and the position (indication value) indicated by the indication input, whether the direction is one of the directions (for example, in the plus direction) or the other one of the directions (for example, in the minus direction) with respect to a predetermined direction. The difference calculating unit 32 inputs the calculated difference to the buffer 34.

The determination unit 33 determines, based on the difference calculated by the difference calculating unit 32, whether the position signal acquired by the position detection unit 100 is abnormal. When the determination unit 33 compares, for example, during drive control of the movable frame 20, the obtained difference with a past difference acquired from the buffer 34, if the difference is almost unchanged even though the movable frame 20 is moving, the difference is equal to or greater than the threshold, and the movable frame 20 has not reached the target position, the determination unit 33 determines that the position signal output from the hall effect sensor 14 is not normal, i.e., determines that the position signal is abnormal. The determination unit 33 inputs the determination result to the drive control unit 35; inputs, if the position signal is normal, the difference to the drive control unit 35 as a driving signal; and inputs, if the position signal is abnormal, the abnormality indication value stored in the storage unit 37 to the drive control unit 35. Furthermore, when determining whether the movable frame 20 is moving, by setting a threshold for the determination, if the difference calculated by the difference calculating unit 32 is equal to or greater than the threshold, the determination unit 33 determines that the movable frame 20 is moving.

The buffer 34 is implemented by using, for example, a ring buffer and stores therein the differences calculated by the difference calculating unit 32 in accordance with time series. If the capacity is insufficient, the buffer 34 stores the latest information in chronological order by overwriting the oldest information by the latest information.

The drive control unit 35 performs drive control of the movable frame 20 by performing control for flowing, in the coils 13A and 13B, the current that is used to maintain the stop position of the movable frame 20 in accordance with the difference calculated by the difference calculating unit 32 or by performing control for flowing, in the coils 13A and 13B, the current that is used to move the movable frame 20 in accordance with the difference calculated by the difference calculating unit 32 or the acquired predetermined value. The drive control unit 35 performs drive control of the movable frame 20 in accordance with the determination result received from the determination unit 33. If the position signal is normal in the determination result, the drive control unit 35 performs, for example, amplification of the driving signal or the adjustment of the phase. The drive control unit 35 performs the drive control (first drive control) of the movable frame 20 by allowing a current to flow in the coils 13A and 13B via the control unit 36 at a current value that is in accordance with the adjusted driving signal. In contrast, if the position signal is abnormal in the determination result, the drive control unit 35 performs the drive control (second drive control) of the movable frame 20 by, for example, acquiring the abnormality indication value (predetermined value) stored in the storage unit 37 and allowing a current to flow in the coils 13A and 13B via the control unit 36 at the current value that is in accordance with the abnormality indication value.

The control unit 36 is formed by using a central processing unit (CPU), or the like and performs drive control of each of the components including the optical unit 2 and performs input/output control of information with respect to each of the components. The control unit 36 sends a signal (current in accordance with the current value) or the like generated by the drive control unit 35 to the optical unit 2 via a predetermined signal line. When the control unit 36 performs automatic focus, the control unit 36 performs control of the movable frame 20 by generating the indication value that indicates the movement position of the movable frame 20 based on the image signal.

The storage unit 37 stores therein data including various programs for operating the optical system 1, various parameters needed to operate the optical system 1, and the like. The storage unit 37 is implemented by a semiconductor memory, such as a flash memory or a dynamic random access Memory (DRAM). Furthermore, the storage unit 37 includes a drive information storage unit 371 that stores therein a threshold that is used by the determination unit 33 to determine whether the position signal is normal, a threshold that is used to determine the position signal has reached the target position (holding at the home position), a threshold that is used to determine whether the movable frame 20 is moving, and an abnormality indication value that is used to perform drive control of the movable frame 20 when the position signal is abnormal.

Figure 5:
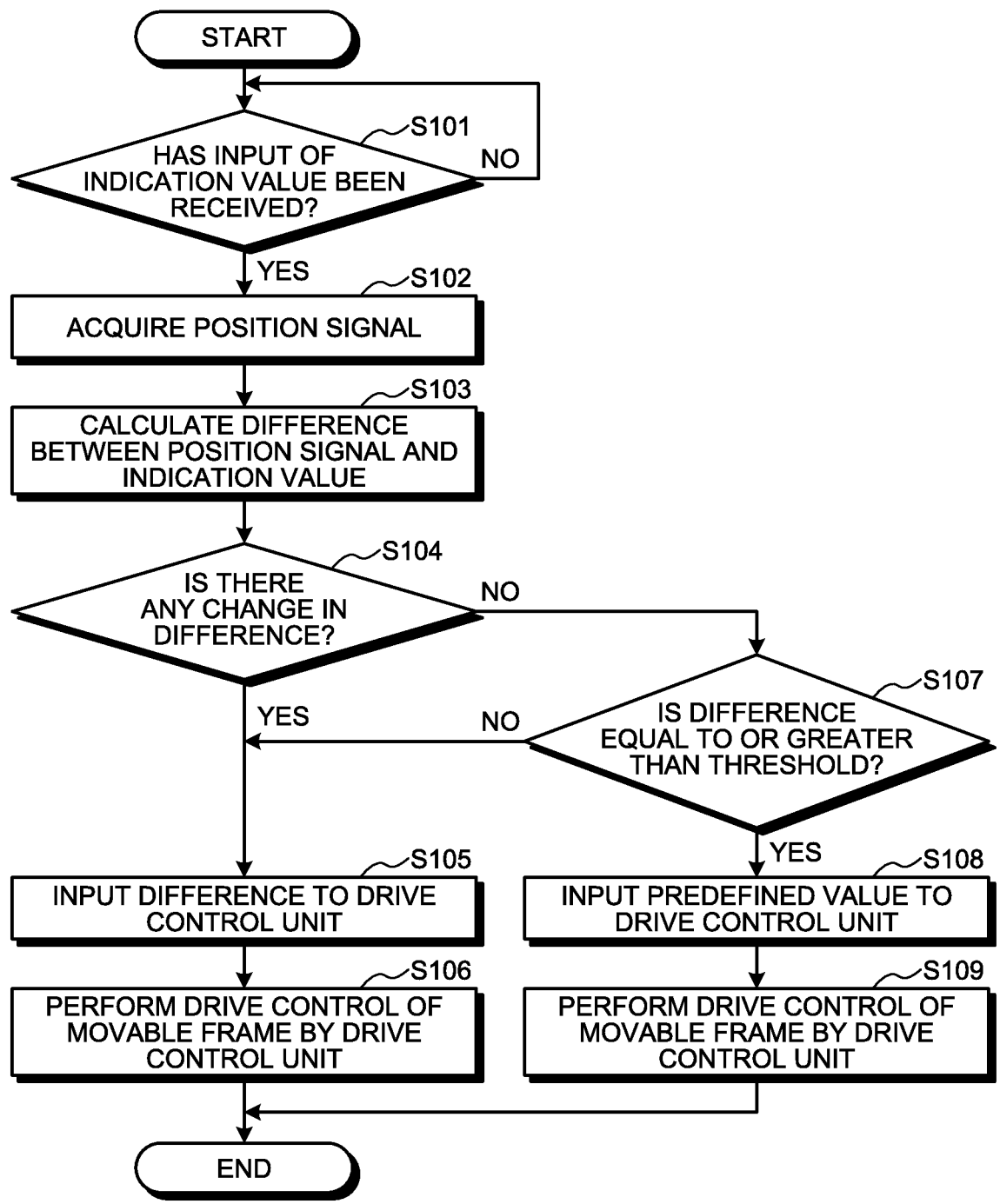
FIG. 5 is a flowchart illustrating a process performed by the optical system according to the first embodiment.

Subsequently, drive control according to the first embodiment will be described with reference to FIG. 5. FIG. 5 is a flowchart illustrating a process performed by the optical system according to the first embodiment. The drive control described below is given with the assumption that an indication value has been input and, if the position signal is normal, control is performed until the movable frame 20 reaches the position in accordance with the indication value (hereinafter, referred to as a target position). Furthermore, in the flowchart, a description will be given by using an example in which the indication value is input via the input unit 31 assuming that manual focus is performed; however, if automatic focus is performed, the control unit 36 generates an indication value.

First, the control unit 36 determines whether an input of the indication value has been received via the input unit 31 (Step S101). If the control unit 36 determines that an input of the indication value has been received (Yes at Step S101), the control unit 36 proceeds to Step S102. In contrast, if the control unit 36 determines that an input of the indication value has not been received (No at Step S101), the control unit 36 repeatedly check an input of the indication value. Alternatively, the control unit 36 may also end the drive control.

At Step S102, the control unit 36 acquires the position signal from the position detection unit 100. The position signal is, as described above, obtained by converting the magnetic field strength detected by the hall effect sensor 14 to a voltage value.

After having acquired the position signal, the difference calculating unit 32 calculates a difference between the position signal (signal value) and the indication value (Step S103). The difference calculating unit 32 inputs the calculated difference to the determination unit 33.

If the difference is input from the difference calculating unit 32, the determination unit 33 determines whether this difference is temporally changed (Step S104). The determination unit 33 acquires a difference that is, for example, a past difference acquired from the buffer 34 and that is calculated immediately before the difference acquired this time; compares the difference calculated this time with the past difference; determines, if the difference has been changed, that the position signal is normal; and determines, if the difference is hardly changed, that the position signal is abnormal. The determination unit 33 determines, based on, for example, the difference between the differences and the thresholds stored in the drive information storage unit 371, whether the position signal is abnormal. The threshold is set based on, for example, the minimum value of the difference between the differences assumed to be minimally changed at the time of the movement of the movable frame 20.

If the determination unit 33 determines that there is a change in difference (Yes at Step S104), the determination unit inputs the difference calculated by the difference calculating unit 32 to the drive control unit 35 as the driving signal (Step S105).

If the difference is input as the driving signal, the drive control unit 35 performs drive control of the movable frame 20 based on the difference (Step S106). Specifically, the drive control unit 35 amplifies the driving signal or adjusts the phase. The drive control unit 35 performs drive control of the movable frame 20 by allowing a current to flow in the coils 13A and 13B via the control unit 36 at the current value that is in accordance with the adjusted driving signal.

In contrast, at Step S104, if the determination unit 33 determines that there is no change in difference (No at Step S104), the determination unit 33 determines whether the difference calculated at Step S103 is equal to or greater than the threshold (Step S107). If the difference is smaller than the threshold (No at Step S107), the determination unit 33 determines that the position signal is normal and the movable frame 20 has reached the target position and proceeds to Step S105. In contrast, if the difference is equal to or greater than the threshold (Yes at Step S107), the determination unit 33 determines that the position signal is abnormal and proceeds to Step S108. The threshold at Step S107 is set based on the difference that is temporally changed (difference in accordance with the movement of the movable frame 20 during home position holding control) at the time of control of the movable frame 20 so as to keep the stop position thereof (home position holding control). Furthermore, if it is determined by the determination unit 33 that the difference is equal to or greater than the threshold (position signal is abnormal), it may also be use a sound, light, an image to report abnormality.

At Step S108, the determination unit 33 refers to the drive information storage unit 371 and inputs the abnormality indication value (predefined signal) to the drive control unit 35 as the driving signal (Step S108).

If the abnormality indication value is input as the driving signal, the drive control unit 35 performs drive control of the movable frame 20 based on this indication value (Step S109). Specifically, the drive control unit 35 performs drive control of the movable frame 20 by allowing the current to flow in the coils 13A and 13B via the control unit 36 at the current value that is in accordance with the driving signal (abnormality indication value). At this time, the abnormality indication value is a value that allows the movable frame 20 to move toward the image sensor side (on the side in which the focal point moves to a far point) and to move to the position in which the movable frame 20 is brought into contact with the stopper (for example, the stopper 26 illustrated in FIG. 4). Namely, if the position signal is abnormal, the drive control unit 35 performs control of the flow of a current that is used to move the movable frame 20 to one of the movable ends in the moving range of the movable frame 20 performed by the voice coil motor.

Even if the position signal becomes abnormal due to the drive control described above and the movable frame 20 is out of control during the driving process, it is possible to move the movable frame 20 to the position in which a certain level of resolution may be maintained. Furthermore, if the movable frame 20 has reached the target position (difference is equal to or less than the threshold), it may also be possible to end the normality/abnormality determination of the position signal and proceeds to perform normal position control of the movable frame 20 or to perform position control by repeating the normality/abnormality determination of the position signal even if the movable frame 20 has reached the target position.

According to the first embodiment described above, if the position signal detected by the position detection unit 100 is normal, drive control of the movable frame 20 is performed by using this position signal and, if the position signal is abnormal, drive control of the movable frame 20 is performed based on the abnormality indication value. Consequently, if the single position detection unit 100 is used and even if it is not able to normally perform position detection of the moving lens, by ensuring a wide field by moving the movable frame 20 such that the focal point is the maximum far point, it is possible to acquire an image having the image quality capable of continuing a treatment given to a subject and, also, suppress an increase in size.

Furthermore, according to the first embodiment, because the detection-purpose magnet 25 is disposed in the vicinity of the main shaft 22 and is disposed on the side surface of the movable frame 20 in the direction orthogonal to the optical axis, even if a portion around the main shaft 22 of the movable frame 20 is affected due to a backlash between main shaft 22 and bearing 24, it is possible to minimize an position detection error.

Furthermore, according to the first embodiment, the movable frame 20 is formed by using a light metal or a heat-resistant resin in order to implement weight reduction compared with a case of using a metal other than a light metal, thus reducing the size of the actuator and consequently downsizing the optical unit 2.

Furthermore, in the first embodiment, a case in which the magnets 12A and 12B are disposed on the fixed frame 10 and the coils 13A and 13B are disposed on the movable frame 20 has been described; however, the coils 13A and 13B may also be disposed on the fixed frame 10 and the magnets 12A and 12B may also be disposed on the movable frame 20.

First Modification of the First Embodiment

Figure 6:
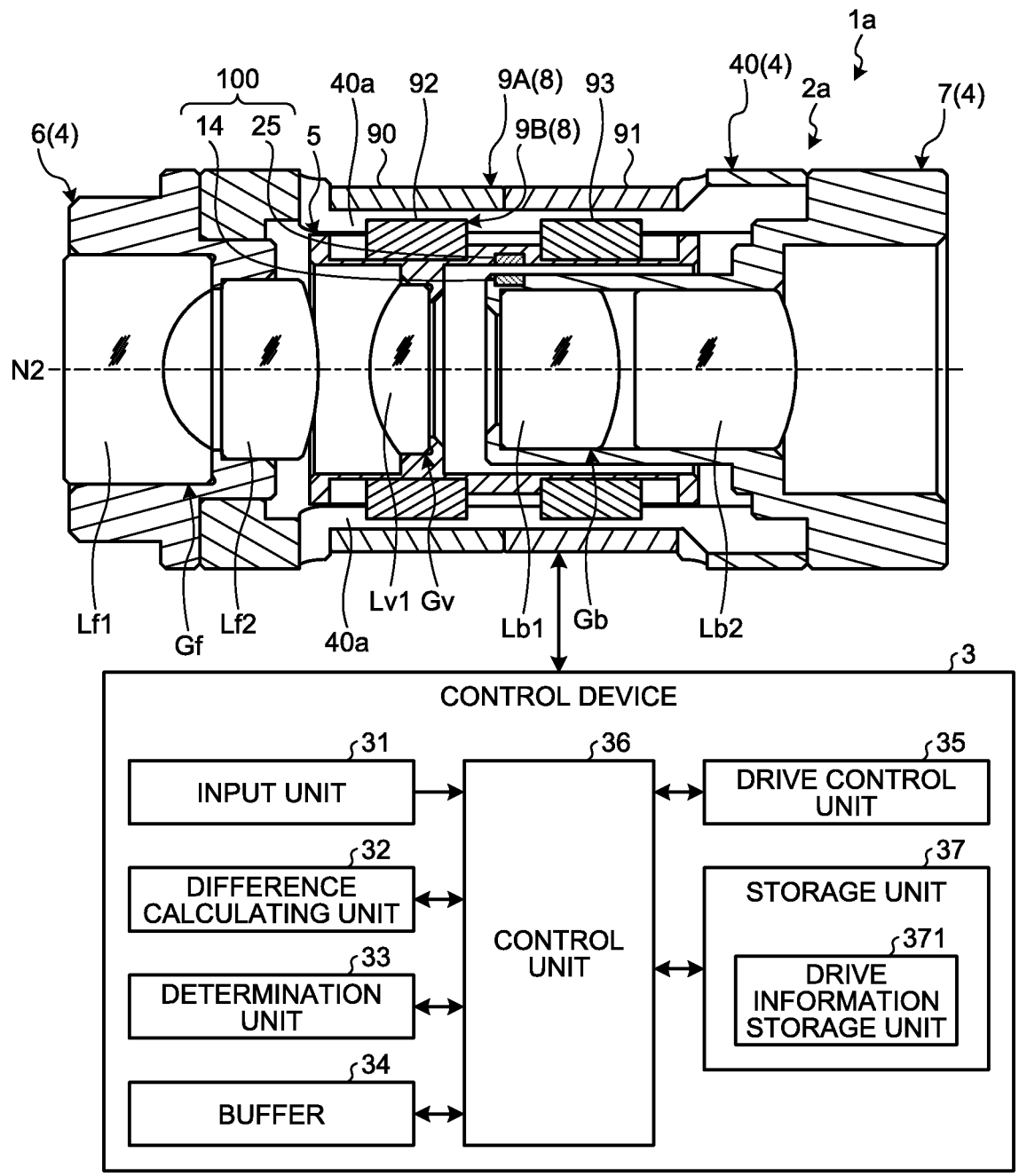
FIG. 6 is a schematic view illustrating, in outline, the configuration of an optical system according to a first modification of the first embodiment.

In the first embodiment described above, a case in which the movable frame 20 is moved along the main shaft 22 has been described; however, the embodiment is not limited to this. For example, the movable frame may also be held by the fixed frame and moved while sliding the inner circumferential surface of the fixed frame. FIG. 6 is a schematic view illustrating, in outline, the configuration of an optical system according to a first modification of the first embodiment and is a partial cross-sectional view of the plane through which the optical axis passes as a section. Furthermore, components that are identical to those described above are assigned the same reference numerals.

An optical system 1a according to the first modification includes an optical unit 2a that may move a lens in the optical axis direction and the control device 3 that performs drive control of each of the components including the optical unit 2a and that performs input/output control of information with respect to each of the components.

The optical unit 2a includes a fixed frame 4 (holding frame), a movable frame 5 that is capable of sliding with respect to the fixed frame 4, and a voice coil motor 8 that generates a driving force that allow the movable frame 5 to move with respect to the fixed frame 4.

The fixed frame 4 includes a fixed frame main body 40; a front frame portion 6 that holds an object-side fixed lens group Gf disposed closer to the object side (near point side) than a moving lens group Gv held by the movable frame 5 and that is attached to the object side of the fixed frame main body 40; and a rear frame portion 7 that holds an image-side fixed lens group Gb closer to the image side (far point side and image sensor side) than the moving lens group Gv and that is attached to the image side of the fixed frame main body 40.

The fixed frame main body 40 is formed of a member having a cylindrical shape with a predetermined axis N2 at the center. In the fixed frame main body 40, a plurality of lightening portions 40a extending in the radial direction is formed.

The front frame portion 6 is a cylindrical member. The front frame portion 6 holds the object-side fixed lens group Gf. The object-side fixed lens group Gf includes a front first lens Lf1 and a front second lens Lf2, which are disposed in this order from the object side. The front frame portion 6 holds the front first lens Lf1 and the front second lens Lf2 by the inner circumferential portion.

The rear frame portion 7 is a cylindrical member. The rear frame portion 7 holds the image-side fixed lens group Gb. The image-side fixed lens group Gb includes a rear first lens Lb1 and a rear second lens Lb2. The rear frame portion 7 holds, in the inner circumferential portion, the rear first lens Lb1 and the rear second lens Lb2 in this order from the object side. Furthermore, the hall effect sensor 14 described above is disposed on the outer circumferential portion of the rear frame portion 7.

The movable frame 5 is a cylindrical member. The movable frame 5 holds the moving lens group Gv. Specifically, the movable frame 5 holds, at the inner circumferential portion, a movable first lens Lv1 included in the moving lens group Gv. Furthermore, at the inner circumferential portion of the movable frame 5, the detection-purpose magnet 25 described above is disposed and the hall effect sensor 14 and the detection-purpose magnet 25 constitute the position detection unit 100.

The movable frame 5 is inserted into the fixed frame main body 40 while a part of the outer circumferential portion of the movable frame 5 is brought into contact with the inner circumferential surface of the fixed frame main body 40. At this time, at least a part of the image-side fixed lens group Gb is present on the inner side of the radial direction of the movable frame 5, i.e., is present inside a hollow space formed by the movable frame 5. In the modification, if the movable frame 5 moves to the most object side, at least a part of the object-side fixed lens group Gf is present in the inner side of the radial direction of the movable frame 5.

The voice coil motor 8 includes, as illustrated in FIG. 6, a coil 9A disposed in the fixed frame main body 40 of the fixed frame 4 and a magnet 9B disposed in the movable frame 5 so as to face the coil 9A.

The coil 9A is formed by disposing two coils 90 and 91 that are wound around the outer circumference of the fixed frame main body 40 in the direction parallel to the axis N2 direction. The two coils disposed adjacent parallel to the axis N2 direction are preferably connected in series but may also be connected in parallel.

Each of a first magnet 92 and a second magnet 93 is disposed on the movable frame 5 so as to be inserted into each of the lightening portions 40a in the fixed frame 4. Each of the first magnet 92 and the second magnet 93 has four magnets disposed parallel to, for example, the circumferential direction. Each of the set of the first magnet 92 and the set of the second magnet 93 is polarized in the radial direction of the movable frame 5 and the magnetic poles are inversely polarized each other.

In the first modification, regarding the coils 90 and 91, it is preferable that the winding direction be inverted between the set of the first magnet 92 and the set of the second magnet 93. Alternatively, it may also be possible to connect the coils 90 and 91 such that the winding directions of the coils 90 and 91 are the same equal and the current directions thereof are inverted. In this case, the directions of the current flowing in the coil 90 and the direction of the current flowing in the coil 91 need to be inverted.

When flowing a current in the coil 9A in the optical unit 2a, due to the effect of the magnetic field of the magnet 9B, the force in the axis N2 direction is generated in the movable frame 5 and the movable frame 5 moves in the axis N2 direction with respect to the fixed frame 4. For example, by controlling the current allowed to flow in the coils 90 and 91, it is possible to move the movable frame 5 with respect to the fixed frame 4.

In also a case in which drive control according to the first embodiment described above is performed by using the optical unit 2a having the configuration described above, if the position signal detected by the position detection unit 100 is normal, drive control of the movable frame 5 is performed by controlling the current applied to the coils 90 and 91 by using this position signal, whereas, if the position signal is abnormal, drive control of the movable frame 5 is performed by controlling the current allowed to flow in the coils 90 and 91 based on the abnormality indication value. If the position signal is abnormal, for example, the movable frame 5 moves such that the movable frame 5 abuts against the rear frame portion 7 based on control of the drive control unit 35. Consequently, in also the optical system 1a, it is possible to maintain, while suppressing an increase in size, the image quality capable of continuing a treatment given to a subject even if position detection of the moving lens is not able to be normally performed.

Second Modification of the First Embodiment

Figure 7:
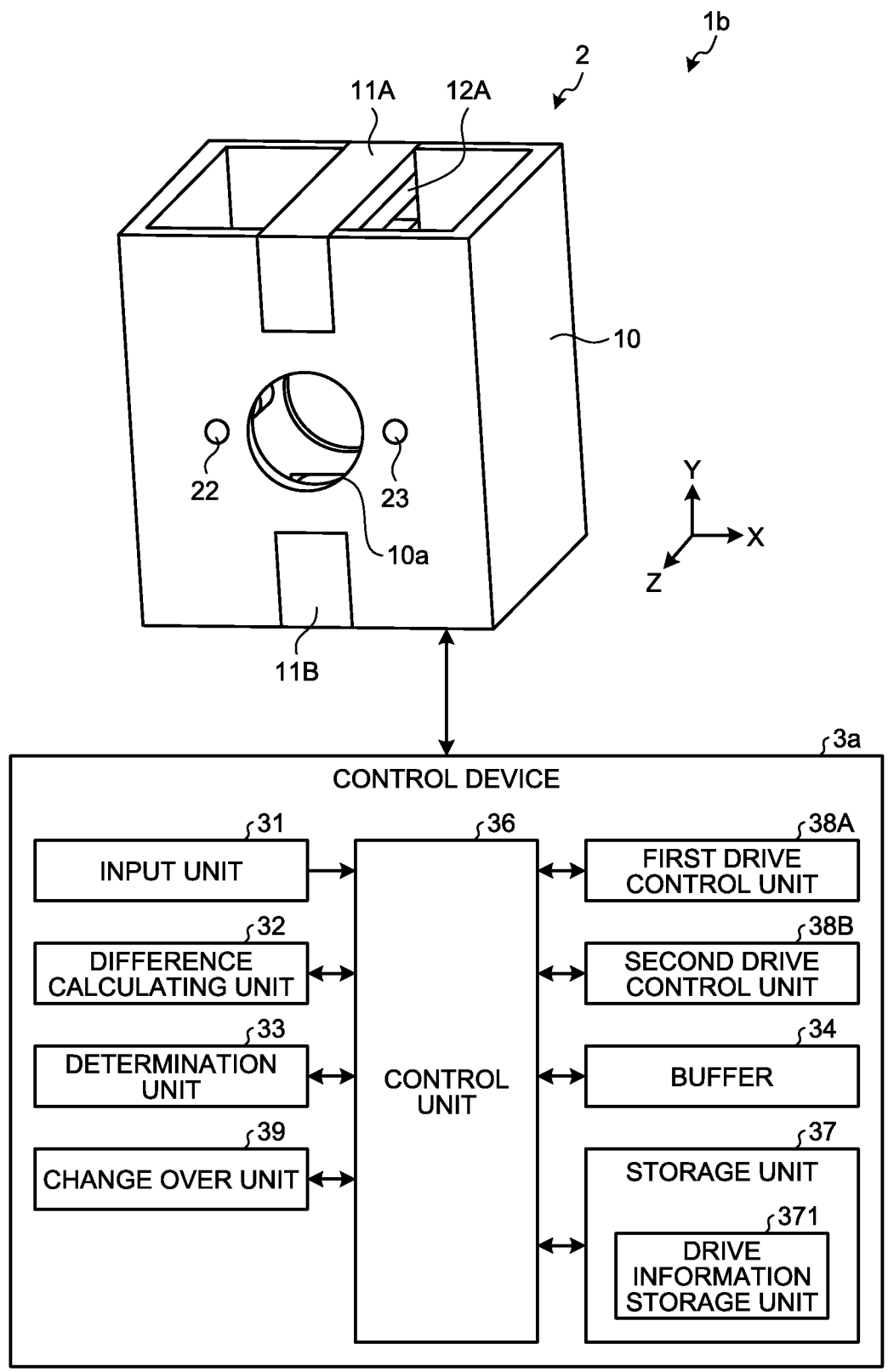
FIG. 7 is a schematic view illustrating, in outline, the configuration of an optical system according to a second modification of the first embodiment.

In the first embodiment described above, a description has been given of a case in which drive control is performed on the movable frame 20 by using the single drive control unit 35; however, the embodiment is not limited to this. For example, a drive control unit may also be formed by a plurality of drive control units having different specifications of drive control and control for driving the movable frame 20 may also be performed. FIG. 7 is a schematic view illustrating, in outline, the configuration of an optical system according to a second modification of the first embodiment. Furthermore, components that are identical to those described above are assigned the same reference numerals.

An optical system 1b according to the second modification includes the optical unit 2 that may move a lens in the optical axis direction and a control device 3a that performs drive control of each of the components including the optical unit 2 and that performs input/output control of information with respect to each of the components. The control device 3a further includes, regarding the configuration of the control device 3 described above, instead of the drive control unit 35, a drive control unit formed by a first drive control unit 38A and a second drive control unit 38B and a change over unit 39.

The first drive control unit 38A performs drive control of the movable frame 20, by performing control for, in accordance with the difference calculated by the difference calculating unit 32, flowing the current that is used to maintain the stop position of the movable frame 20 in the coils 13A and 13B or flowing the current that is used to move the movable frame 20 in the coils 13A and 13B. If the determination result obtained by the determination unit 33 indicates that the position signal is normal, the first drive control unit 38A performs drive control of the movable frame 20. If the position signal is normal in the determination result, the first drive control unit 38A performs, for example, amplification of the driving signal or adjustment of the phase. The first drive control unit 38A performs drive control of the movable frame 20 by flowing the current is allowed to flow in the coils 13A and 13B via the control unit 36 with the current value that is in accordance with the adjusted driving signal.

The second drive control unit 38B performs drive control of the movable frame 20 by moving the movable frame 20 by flowing the current with a predetermined value in the coils 13A and 13B. The second drive control unit 38B performs drive control of the movable frame 20 when the determination result obtained by the determination unit 33 indicates that the position signal is abnormal. If the position signal in the determination result is abnormal, the second drive control unit 38B performs drive control of the movable frame 20 by, for example, acquiring an abnormality indication value stored in the drive information storage unit 371 and flowing the current in the coils 13A and 13B via the control unit 36 at the current value that is in accordance with the abnormality indication value. At this time, the abnormality indication value is a value that allows the movable frame 20 to move toward the image sensor side (on the side in which the focal point moves to a far point) and to move to the position in which the movable frame 20 is brought into contact with the stopper (for example, the stopper 26 or 27 illustrated in FIG. 4). Namely, if the position signal is abnormal, the second drive control unit 38B performs control of the flow of a current used to move the movable frame 20 to one of the movable ends in the moving range of the movable frame 20 performed by the voice coil motor.

The change over unit 39 changes the drive control unit that performs drive control of the movable frame 20 in accordance with the determination result obtained from the determination unit 33.

Figure 8:
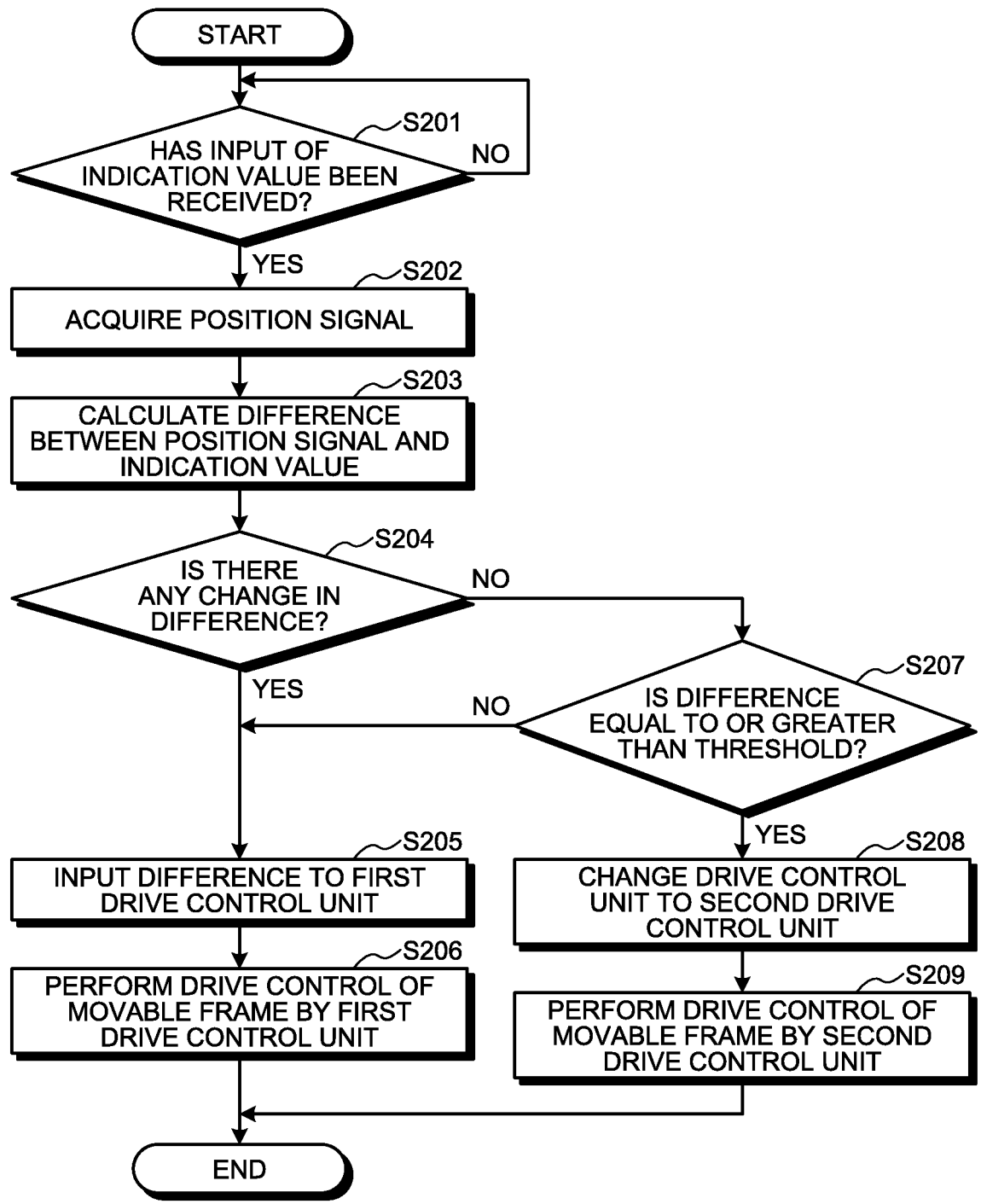
FIG. 8 is a flowchart illustrating a process performed by the optical system according to the second modification of the first embodiment.

FIG. 8 is a flowchart illustrating a process performed by the optical system according to the second modification of the first embodiment. Furthermore, in the flowchart described below, as the initial setting, a description will be given with the assumption that the first drive control unit 38A is set in the drive control unit that performs drive control of the movable frame 20. Furthermore, in also the flowchart, an example in which an indication value is input via the input unit 31 will be described assuming that manual focus is performed; however, in the case where automatic focus is performed, the control unit 36 generates an indication value.

First, the control unit 36 determines whether an input of the indication value has been received via the input unit 31 (Step S201). If the control unit 36 determines that an input of the indication value has been received (Yes at Step S201), the control unit 36 proceeds to Step S202. In contrast, if the control unit 36 determines that an input of the indication value has not been received (No at Step S201), the control unit 36 repeatedly checks an input of the indication value or ends drive control.

At Step S202, the control unit 36 acquires the position signal from the position detection unit 100. After having acquired the position signal, the difference calculating unit 32 calculates a difference between the signal value of the position signal and the indication value (Step S203). The difference calculating unit 32 inputs the calculated difference to the determination unit 33.

If the difference is input from the difference calculating unit 32, the determination unit 33 determines whether this difference is temporally changed (Step S204). Here, if it is determined, by the determination unit 33, that the difference has been changed (Yes at Step S204), the determination unit 33 inputs the difference calculated by the difference calculating unit 32 to the first drive control unit 38A as the driving signal (Step S205).

If the difference is input as the driving signal, the first drive control unit 38A performs drive control of the movable frame 20 based on the subject difference (Step S206). Specifically, the first drive control unit 38A amplifies the driving signal or adjusts the phase. The first drive control unit 38A performs drive control of the movable frame 20 by flowing the current in the coils 13A and 13B via the control unit 36 at the current value that is in accordance with the adjusted driving signal.

In contrast, if the determination unit 33 determines, at Step S204, that there is no change in difference (No at Step S204), the determination unit 33 determines whether the difference calculated at Step S203 is equal to or greater than the threshold (Step S207). If the difference is smaller than the threshold (No at Step S207), the determination unit 33 determines that the position signal is normal and the movable frame 20 has reached the target position and proceeds to Step S205. In contrast, if the difference is equal to or greater than the threshold (Yes at Step S207), the determination unit 33 determines that the position signal is abnormal and proceeds to Step S208.

At Step S208, the change over unit 39 changes the drive control unit that performs drive control of the movable frame 20 from the first drive control unit 38A to the second drive control unit 38B (Step S208). Furthermore, if the drive control unit is changed to the second drive control unit 38B by the change over unit 39, the control unit 36 refers to the drive information storage unit 371 and inputs the abnormality indication value (predefined signal) to the second drive control unit 38B as the driving signal. Alternatively, if the drive control unit is changed to the second drive control unit 38B by the change over unit 39, the second drive control unit 38B performs the drive control of the movable frame 20 by performing control of the flow of the current with the specified current value in the coils 13A and 13B via the control unit 36 regardless of the difference between the position signal and the indication value.

If the abnormality indication value is input as the driving signal, the second drive control unit 38B performs drive control of the movable frame 20 based on the subject indication value (Step S209). Specifically, the second drive control unit 38B performs drive control of the movable frame 20 by flowing the current in the coils 13A and 13B via the control unit 36 at the current value that is in accordance with the driving signal (abnormality indication value).

With the drive control described above, even if abnormality is generated in the position signal and the movable frame 20 is out of control during a driving process, it is possible to move, due to control of the second drive control unit 38B, the movable frame 20 to the position in which a certain resolution is maintained.

Second Embodiment

Figure 9:
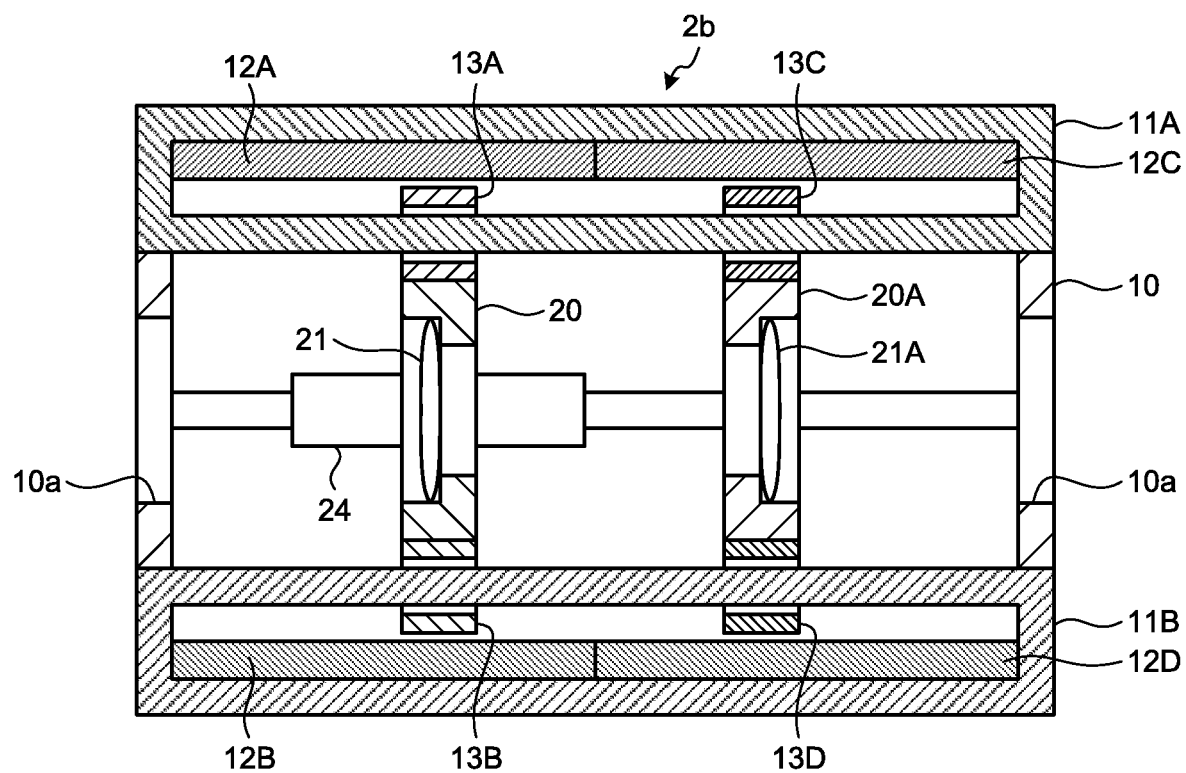
FIG. 9 is a partial cross-sectional view illustrating a relevant part of an optical system according to a second embodiment.
Figure 10:
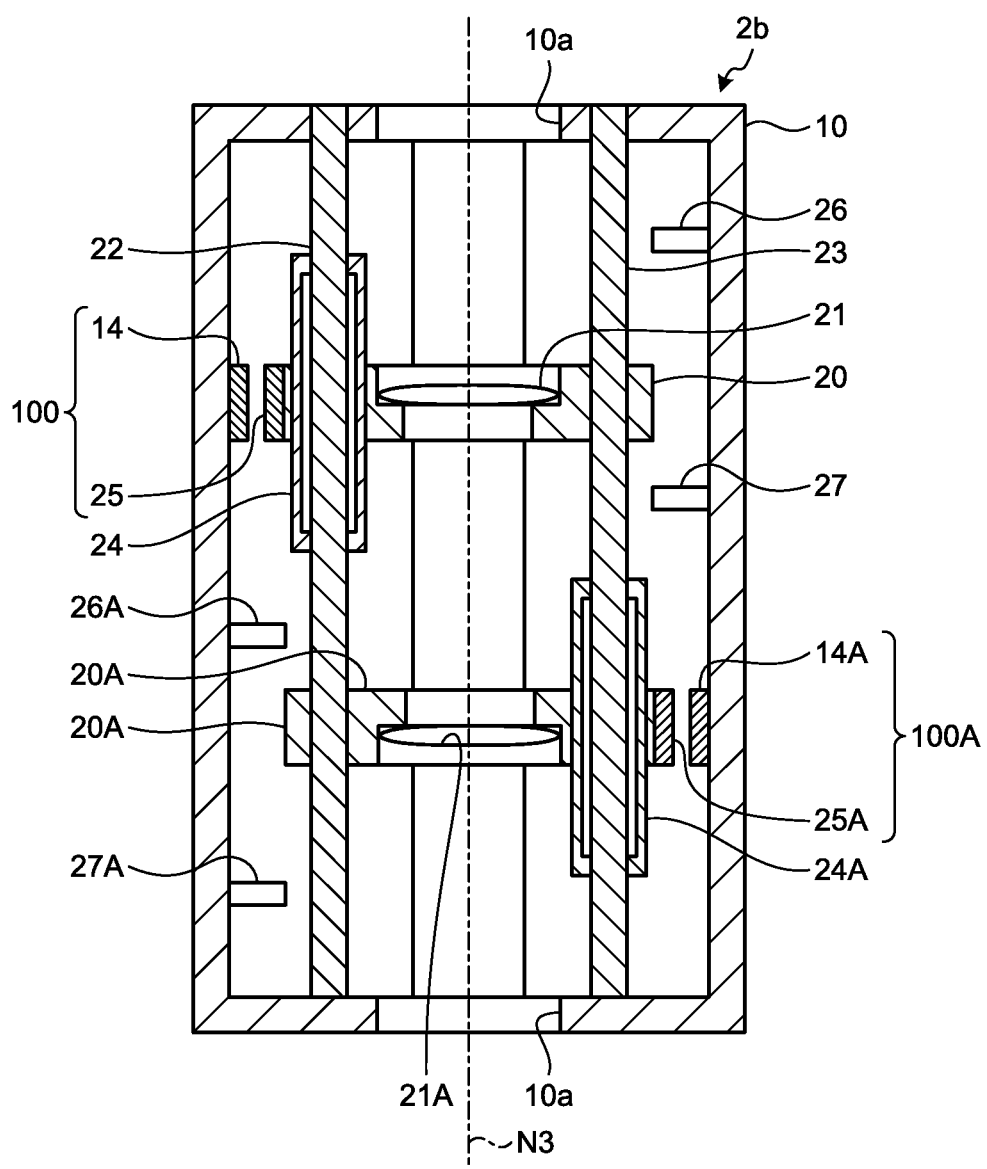
FIG. 10 is a partial cross-sectional view illustrating a relevant part of the optical system according to the second embodiment.
Figure 11:
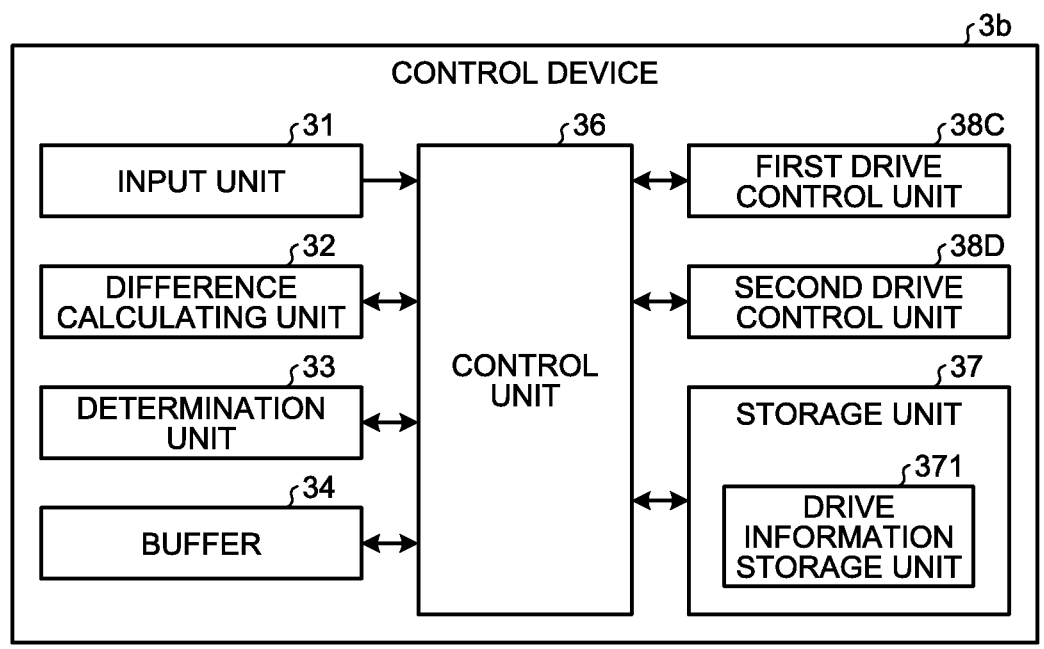
FIG. 11 is a block diagram illustrating the configuration of a relevant part of the optical system according to the second embodiment.

In the first embodiment described above, a case in which the optical unit 2 performs drive control of the single movable frame 20 has been described; however, the embodiment is not limited to this. For example, a plurality of movable frames that may individually move may also be used. FIG. 9 is a partial cross-sectional view, associated with line B-B in FIG. 1, illustrating a relevant part of an optical system according to a second embodiment. FIG. 10 is a partial cross-sectional view, associated with line C-C in FIG. 1, illustrating a relevant part of the optical system according to the second embodiment. FIG. 11 is a block diagram illustrating the configuration of a relevant part of the optical system according to the second embodiment. Furthermore, components that are identical to those described above are assigned the same reference numerals.

An optical system according to the second embodiment includes an optical unit 2b that may move a lens in the optical axis direction and a control device 3b that performs drive control of each of the components including the optical unit 2b and that performs input/output control of information with respect to each of the components.

The optical unit 2b includes, in addition to the configuration of the optical unit 2, a second movable frame 20A, a second moving lens 21A, a bearing 24A, second stoppers 26A and 27A, a second position detection unit 100A that includes a second hall effect sensor 14A and a second detection-purpose magnet 25A, and a second voice coil motor that includes second magnets 12C and 12D and second coils 13C and 13D. Hereinafter, the movable frame 20 is referred to as the first movable frame 20; the moving lens 21 is referred to as the first moving lens 21; the hall effect sensor 14 is referred to as the first hall effect sensor 14; the detection-purpose magnet 25 is referred to as the first detection-purpose magnet 25; the stoppers 26 and 27 are referred to as the first stoppers 26 and 27, respectively; the position detection unit 100 is referred to as the first position detection unit 100; the magnets 12A and 12B are referred to as the first magnets 12A and 12B, respectively; and the coils 13A and 13B are referred to as the first coils 13A and 13B, respectively. In the second embodiment, the two movable frames 20 and 20A may individually move along the main shaft 22 (in the direction of an optical axis N3 of each of the moving lenses 21 and 21A). Furthermore, the first hall effect sensor 14 outputs the first position signal and the second hall effect sensor 14A outputs the second position signal. In the following, a description will be given with the assumption that both the moving lenses 21 and 21A are focus lenses.

The control device 3b includes, regarding the configuration of the control device 3 described above, instead of the drive control unit 35, a drive control unit formed by a first drive control unit 38C and a second drive control unit 38D. Furthermore, regarding each of the first position signal and the second position signal, the determination unit 33 performs determination of normality/abnormality.

The first drive control unit 38C performs drive control of the first movable frame 20 in accordance with the determination result obtained from the determination unit 33. If the position signal is normal in the determination result, the first drive control unit 38C performs, for example, amplification of the driving signal or adjustment of the phase. The first drive control unit 38C performs drive control (the first drive control) of the first movable frame 20 by flowing a current in the first coils 13A and 13B via the control unit 36 with the current value that is in accordance with the adjusted driving signal. In contrast, if the position signal is abnormal in the determination result, the first drive control unit 38C performs drive control (the second drive control) of the first movable frame 20 by, for example, acquiring the abnormality indication value stored in the drive information storage unit 371 and flowing the current in the first coils 13A and 13B via the control unit 36 with the current value that is in accordance with the abnormality indication value.

The second drive control unit 38D performs drive control of the second movable frame 20A in accordance with the determination result obtained from the determination unit 33. If the position signal is normal in the determination result, the second drive control unit 38D performs, for example, amplification of the driving signal or adjustment of the phase. The second drive control unit 38D performs drive control (the third drive control) of the second movable frame 20A by flowing the current in the second coils 13C and 13D via the control unit 36 with the current value that is in accordance with the adjusted driving signal. In contrast, if the position signal is abnormal in the determination result, the second drive control unit 38D performs drive control (the fourth drive control) of the second movable frame 20A by, for example, acquiring the abnormality indication value stored in the drive information storage unit 371 and flowing the current in the second coils 13C and 13D via the control unit 36 with the current value that is in accordance with the abnormality indication value.

Figure 12:
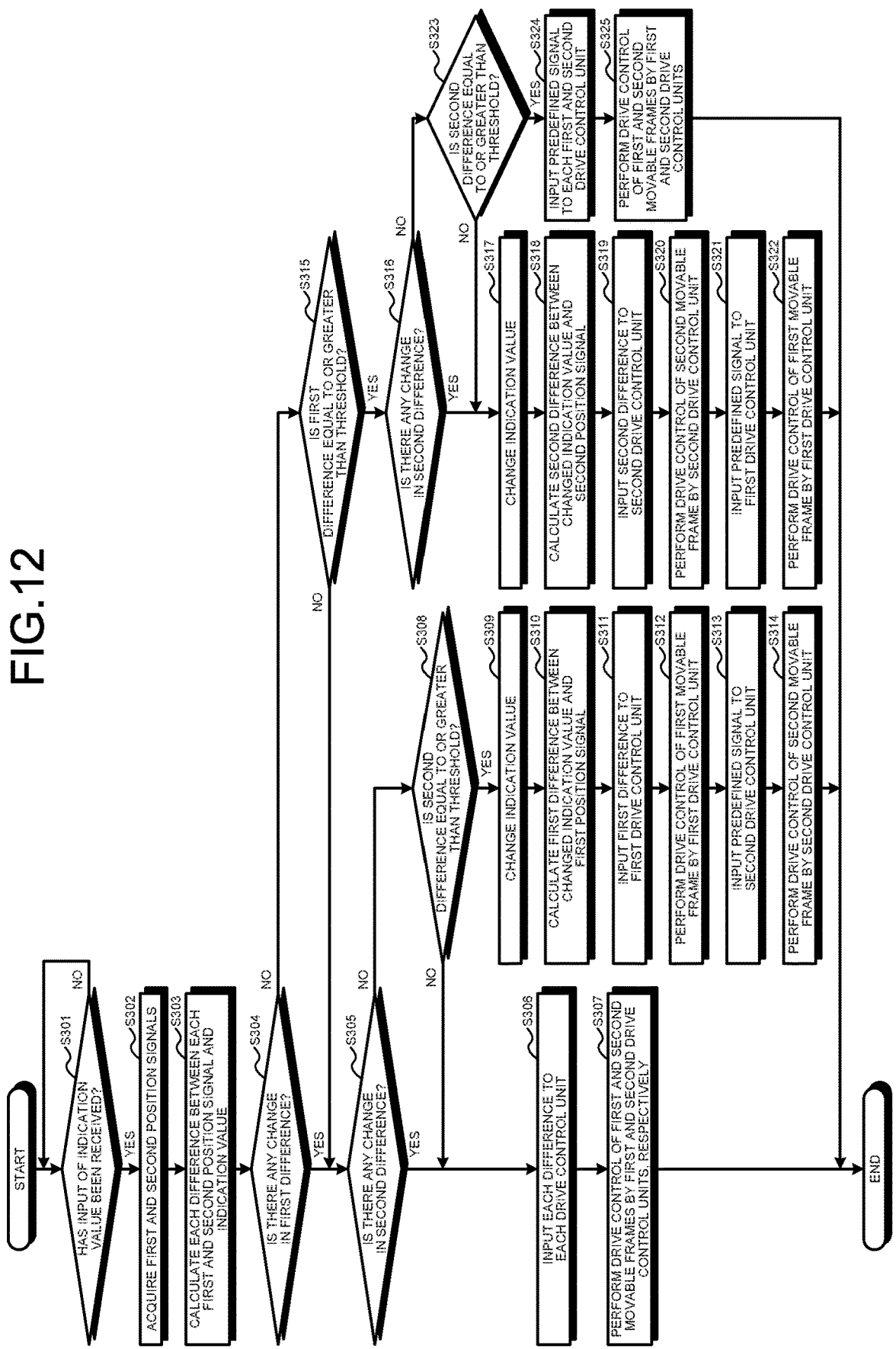
FIG. 12 is a flowchart illustrating a process performed by the optical system according to the second embodiment.

In the following, the drive control according to the second embodiment will be described with reference to FIG. 12. FIG. 12 is a flowchart illustrating a process performed by the optical system according to the second embodiment. A description will be given with the assumption that the drive control performs control, if an indication value has been input and the position signal is normal, until the first movable frame 20 and the second movable frame 20A have reached the position that is in accordance with the indication value (hereinafter, referred to as a target position). Furthermore, in also the flowchart, an example in which a first and a second indication signals (indication values) with respect to the first movable frame 20 and the second movable frame 20A, respectively, are input via the input unit 31 will be described assuming that manual focus is performed; however, in the case where automatic focus is performed, the control unit 36 generates the first and the second indication values with respect to the first movable frame 20 and the second movable frame 20A, respectively.

First, the control unit 36 determines whether an input of the indication value has been received via the input unit 31 (Step S301). If the control unit 36 determines that an input of the indication value has been received (Yes at Step S301), the control unit 36 proceeds to Step S302. In contrast, if the control unit 36 determines that an input of the indication value has not been received (No at Step S301), the control unit 36 repeatedly checks an input of the indication value or ends drive control. Furthermore, in the indication value that is input in the second embodiment, the indication value indicating each of the positions of the movements of the first movable frame 20 and the second movable frame 20A move is included. A combination of the positions of the movements of the first movable frame 20 and the second movable frame 20A (indication values) is stored in the storage unit 37 (or the drive information storage unit 371) in association with the indication signals that are input via the input unit 31.

At Step S302, the control unit 36 acquires the first and the second position signal from the first position detection unit 100 and the second position detection unit 100A, respectively. After having acquired the first and the second position signals, the difference calculating unit 32 calculates each of the differences between the signal values of the first and the second position signals and the indication value (the first and the second differences) (Step S303). The difference calculating unit 32 inputs the calculated first and the second differences to the determination unit 33.

If the first and the second differences are input from the difference calculating unit 32, first, the determination unit 33 determines whether the first difference is temporally changed (Step S304). If the determination unit 33 determines that the first difference is temporally changed (Yes at Step S304), the determination unit 33 determines that the first position signal is normal and then determines whether the second difference is temporally changed (Step S305).

Here, if the determination unit 33 determines that the second difference is changed (Yes at Step S305), the determination unit 33 inputs the first difference to the first drive control unit 38C as the driving signal and input the second difference to the second drive control unit 38D as the driving signal (Step S306).

If the first and the second differences are input as the driving signals, the first drive control unit 38C and the second drive control unit 38D perform drive control of the first movable frame 20 and the second movable frame 20A, respectively, based on the first and the second differences (Step S307).

In contrast, if the determination unit 33 determines, at Step S305, that the second difference is not changed (No at Step S305), the determination unit 33 determines whether the second difference calculated at Step S303 is equal to or greater than the threshold (Step S308). If the second difference is smaller than the threshold (No at Step S308), the determination unit 33 determines that the second position signal is normal and the movable frame 20 has reached the target position and proceeds to Step S306. In contrast, if the second difference is equal to or greater than the threshold (Yes at Step S308), the determination unit 33 determines that the second position signal is abnormal and proceeds to Step S309.

At Step S309, the determination unit 33 changes the indication value (Step S309). Regarding the changed indication value in this case, the indication value with respect to the second movable frame 20A corresponds to the abnormality indication value used to move to the moving end on the opposite side of the side of the first movable frame 20 (for example, the second stopper 27A) and the indication value with respect to the first movable frame 20 corresponds to the value used to move to the focal position at a far point at the time of the second movable frame 20A being moved to the moving end described above. Furthermore, a far point does not always correspond to the opposite side of the side of the first movable frame 20 and moves to, in some cases, depending on an optical system, the first movable frame 20 side. Furthermore, the direction of the movement of the movable frame is determined in accordance with the positional relationship among the optical unit 2, the image sensor, and an object or the setting of the movable frame to be moved to which side between the far point side and the near point side.

If the determination unit 33 changes the indication value at Step S309, the difference calculating unit 32 calculates the first difference between the changed indication value and the first position signal (Step S310). Then, the difference calculating unit 32 inputs the first difference calculated at Step S310 to the first drive control unit 38C as the driving signal (Step S311).

If the first difference is input as the driving signal, the first drive control unit 38C performs drive control of the first movable frame 20 based on the first difference (Step S312).

At Step S313, the determination unit 33 inputs the abnormality indication value (predefined signal) to the second drive control unit 38D as the driving signal. If the abnormality indication value is input, the second drive control unit 38D performs drive control of the second movable frame 20A based on the indication value (Step S314). Furthermore, the processes at Steps S313 and S314 may also be performed before or in parallel with Step S310.

Furthermore, if the determination unit 33 determines that, at Step S304, the first difference is not changed (No at Step S304), the determination unit 33 determines whether the first difference calculated at Step S303 is equal to or greater than the threshold (Step S315). If the first difference is smaller than the threshold (No at Step S315), the determination unit 33 determines that the first position signal is normal and the movable frame 20 has reached the target position and proceeds to Step S305. In contrast, if the first difference is equal to or greater than the threshold (Yes at Step S315), the determination unit 33 determines that the first position signal is abnormal and proceeds to Step S316.

At Step S316, the determination unit 33 determines whether the second difference is temporally changed (Step S316). Here, if the determination unit 33 determines that the second difference is changed (Yes at Step S316), the determination unit 33 proceeds to Step S317, whereas, if the second position signal is not changed (No at Step S316), the determination unit 33 proceeds to Step S323.

At Step S317, the determination unit 33 changes the indication value (Step S317). Regarding the changed indication value in this case, the indication value with respect to the first movable frame 20 corresponds to the abnormality indication value used to move to the moving end on the opposite side of the side of the second movable frame 20A (for example, the first stopper 26) and the indication value with respect to the second movable frame 20A corresponds to the value used to move to the focal position at a far point at the time of the first movable frame 20 being moved to the moving end described above. Furthermore, also regarding Step S317, similarly to Step S309 described above, a far point does not always correspond to the opposite side of the side the first movable frame 20 and moves to, in some cases, depending on an optical system, the first movable frame 20 side. The direction of the movement of the movable frame is determined in accordance with the positional relationship among the optical unit 2, the image sensor, and an object or the setting of the movable frame to be moved to which side between the far point side and a near point side.

If the determination unit 33 changes the indication value at Step S317, the difference calculating unit 32 calculates the second difference between the changed indication value and the second position signal (Step S318). Then, the difference calculating unit 32 inputs the second difference calculated at Step S318 to the second drive control unit 38D as the driving signal (Step S319).

If the second difference is input as the driving signal, the second drive control unit 38D performs drive control of the second movable frame 20A based on the second difference (Step S320).

At Step S321, the determination unit 33 inputs the abnormality indication value (predefined signal) to the first drive control unit 38C as the driving signal. If the abnormality indication value is input, the first drive control unit 38C performs drive control of the first movable frame 20 based on the indication value (Step S322). Furthermore, the processes at Steps S321 and S322 may also be performed before or in parallel with Step S318.

Furthermore, at Step S323, it is determined whether the second difference calculated at Step S303 is equal to or greater than the threshold (Step S323). If the second difference is smaller than the threshold (No at Step S323), the determination unit 33 determines that the second position signal is normal and the movable frame 20 has reached the target position and proceeds to Step S317. In contrast, if the second difference is equal to or greater than the threshold (Yes at Step S323), the determination unit 33 determines that the second position signal is abnormal and proceeds to Step S324.

At Step S324, the determination unit 33 changes the input indication value to the abnormality indication value in the case where the two position signals (the first and the second position signals) are abnormal and inputs the changed indication value to each of the first drive control unit 38C and the second drive control unit 38D (Step S324). The indication value at this time may also be the value that is set as the indication value in the case where the first and the second position signals are abnormal or may also be set to the indication value at Step S309 or S317.

If the abnormality indication value is input, the first drive control unit 38C and the second drive control unit 38D perform drive control of the first movable frame 20 and the second movable frame 20A, respectively, based on the indication value (Step S325).

Even if, due to the drive control described above, abnormality occurs in the position signal and the first movable frame 20 and/or the second movable frame 20A is out of control during the driving process, it is possible to move the first movable frame 20 and the second movable frame 20A to the position in which a certain resolution is maintained.

With the second embodiment according to the present disclosure, if the position signal detected by the position detection unit 100 is normal, drive control of the first movable frame 20 and/or the second movable frame 20A is performed by using this position signal and, if the position signal is abnormal, drive control of the first movable frame 20 and/or the second movable frame 20A is performed based on the abnormality indication value; therefore, even if the movable frames are used and position detection of the moving lens of at least one of the movable frames is not able to be normally performed, by ensuring a wide field by moving the first movable frame 20 and/or the second movable frame 20A such that the focal point corresponds to the maximum far point, it is possible to acquire an image having the image quality capable of continuing a treatment given to a subject and, also, suppress an increase in size.

Furthermore, in the second embodiment described above, the control device 3a may be used instead of the control device 3b. In this case, each of the first and the second drive control units includes a drive control unit that controls the movable frame in accordance with normality/abnormality of the position signal, the drive control unit that performs drive control of each of the first and the second drive control units is changed by the change over unit 39, and the first movable frame 20 and the second movable frame 20A are controlled.

Furthermore, in the second embodiment described above, if it is determined that the first position signal is abnormal at Step S304, if at least one of the position signals is abnormal, it may also be possible to perform control such that at least one of the movable frames is disposed at a predetermined position by changing the indication value with respect to each of the movable frames to a predetermined value and by moving the movable frame to the previously set position.

Furthermore, in the second embodiment described above, a description has been given with the assumption that both the moving lenses 21 and 21A are focus lenses; however, for example, in the case where the moving lens 21 is used as a focus lens, the moving lens 21A is used as a zoom lens, the first indication signal is normal, and the second indication signal is abnormal, the indication value with respect to the second movable frame 20A corresponds to the abnormality indication value used to move to the moving end at the opposite side of the side of the first movable frame 20 (for example, the second stopper 27A corresponding to the wide angle end) and the indication value with respect to the first movable frame 20 corresponds to the value used to move to the focal position at a far point at the time of the second movable frame 20A being moved to the moving end (wide angle end) described above. In addition, for example, in the case where both the moving lenses 21 and 21A are used as zoom lenses, the first indication signal is normal, and the second indication signal is abnormal, the indication value with respect to the second movable frame 20A corresponds to the abnormality indication value used to move to the moving end on the opposite side of the side of the first movable frame 20 (for example, the second stopper 27A corresponding to the wide angle end) and the indication value with respect to the first movable frame 20 corresponds to the value used to move to the focal position at a wide angle at the time of the second movable frame 20A being moved to the moving end (wide angle end).

Furthermore, in the second embodiment described above, a case in which two movable frames and moving lenses are included has been described; however, three or more movable frames and moving lenses may also be included. Even if three or more movable frames and moving lenses are used, drive control of each of the movable frames is performed based on the positional relationship of the moving lens determined at the time of abnormality.

Here, in the first and the second embodiments and the first and the second modifications, by flowing the current having the abnormality indication value that momentarily exceeds a specified value, it is possible to drive the movable frame 20 even in the case of poor sliding of the movable frame 20, not limited to the case of a failure of the hall effect sensor 14.

Furthermore, in the first and the second embodiments and the first and the second modifications, a case in which the hall effect sensor is provided on the fixed frame side and the detection-purpose magnet is provided on the movable frame side has been described; however, the detection-purpose magnet may also be provided on the fixed frame side and the hall effect sensor may also be provided on the movable frame side.

Furthermore, in the first and the second embodiments and the first and the second modifications, an example of the configuration in which the determination unit is provided separated from the control unit has been described as an example; however, the determination unit is provided in the control unit.

Furthermore, in the first and the second embodiments and the first and the second modifications, a case in which the hall effect sensor is used as a position detection sensor has been described as an example; however, the position may also be detected by using an MR sensor.

Furthermore, in the first and the second embodiments and the first and the second modifications, position detection may also be performed by using a magnet of the voice coil motor instead of providing the detection-purpose magnet.

Furthermore, in the first and the second embodiments and the first and the second modifications, the disposition of the magnet and the coil in the voice coil motor may also be inverted.

Furthermore, in the first embodiment and the modifications described above, a description has been given of a case in which the hall effect sensor sequentially converts the detected magnetic field strength to a voltage value and the voltage values based on the magnetic field strength are output to the control device as the position signals; however, the magnetic field strength may also be output to the control device as a position signal. In this case, each of the voltage values is calculated instead of the magnetic field strength.

Third Embodiment

Figure 13:
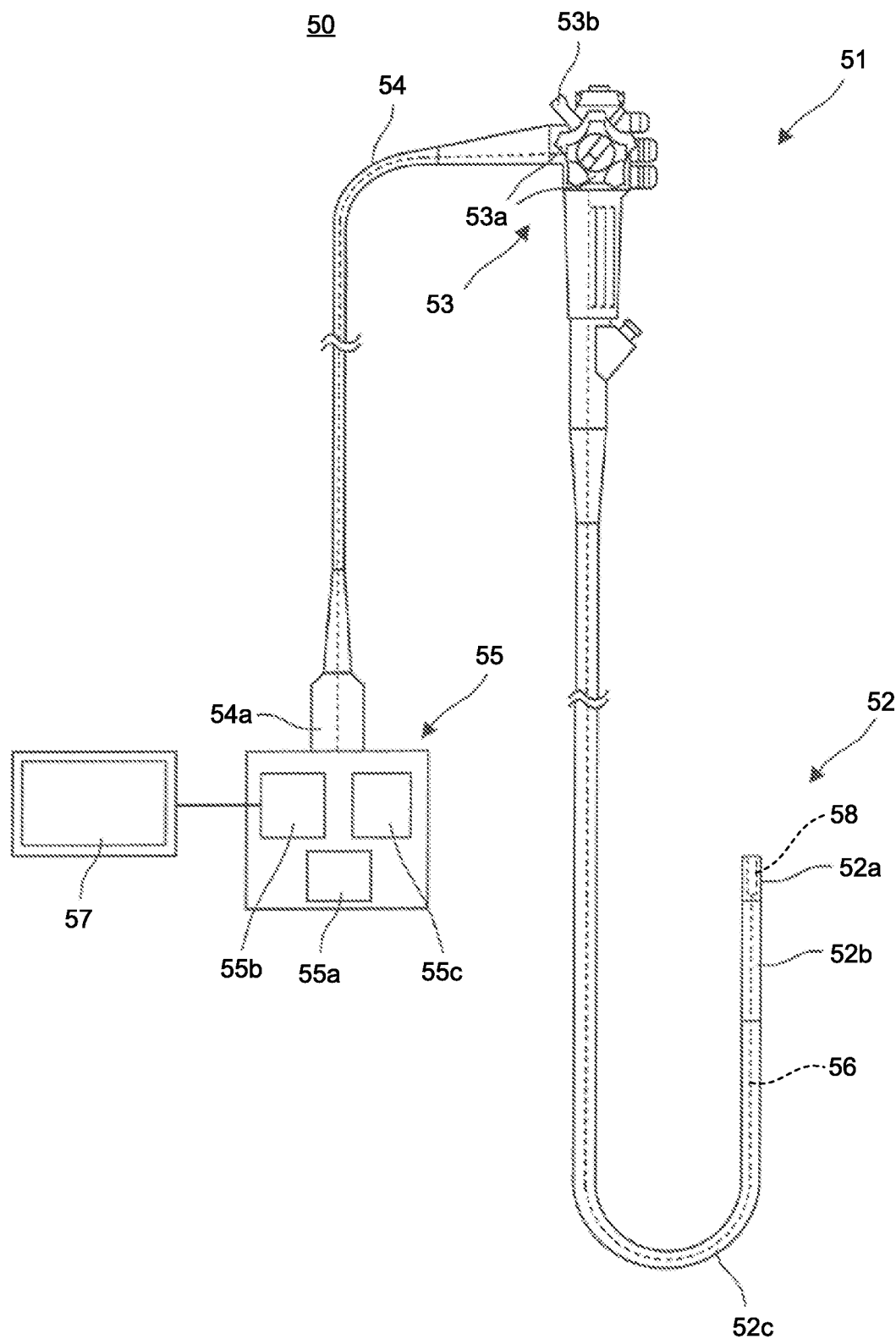
FIG. 13 is a diagram illustrating the configuration of an endoscope system provided with an endoscope according to a third embodiment.

FIG. 13 is a diagram illustrating the configuration of an endoscope system provided with an endoscope according to a third embodiment. An endoscope system 50 illustrated in FIG. 13 includes an endoscope 51, a control device 55, and a display device 57. The endoscope 51 includes one of the optical systems 1 and 1a according to the first embodiment or the modification described above. In the following, a description will be given of a case of having the optical system 1 (the optical unit 2) as an example.

The endoscope 51 may be introduced into a subject, such as a human body, and optically captures a predetermined observed region inside the subject. Furthermore, the subject in which the endoscope 51 is introduced is not limited to a human body and another living body or an artificial material, such as a machine or a building, may also be used. In other words, the endoscope 51 may also be a medical endoscope or an industrial endoscope.

The endoscope 51 includes an insertion portion 52 that is introduced into a subject, an operating unit 53 located at the proximal end of the insertion portion 52, and a universal code 54 as a composite cable extending from the operating unit 53.

The insertion portion 52 includes a distal end portion 52a disposed at the distal end; a curved section 52b that is freely bendable and is disposed on the proximal end side of the distal end portion 52a; and a flexible tube 52c that is disposed on the proximal end side of the curved section 52b, that is connected to the distal end side of the operating unit 53, and that has flexibility. At the distal end portion 52a, an imaging unit 58 that condenses light from an object and that captures the object is provided. The imaging unit 58 includes the optical unit 2 that condenses light from the object and an image sensor that photoelectrically converts the light condensed by the optical unit 2 and that outputs the light. Furthermore, the endoscope 51 may also be a rigid endoscope that does not have the flexible tube 52c in the insertion portion 52.

The operating unit 53 includes an angle operating unit 53a that operates a curved state of the curved section 52b and an optical unit operating unit 53b that designates the operation of the voice coil motors 30A and 30B described above and that performs a zoom operation or a focusing operation in the optical unit 2. The angle operating unit 53a is formed in a knob shape and the optical unit operating unit 53b is formed in a lever shape; however, the operating units may also be another type, such as a volume switch or a push switch.

The universal code 54 is a member that connects the operating unit 53 and the control device 55. The endoscope 51 is connected to the control device 55 via a connector 54a disposed at the proximal end portion of the universal code 54.

In the insertion portion 52, the operating unit 53, and the universal code 54, a cable 56, such as a wire, an electrical wire, or an optical fiber, is inserted.

The control device 55 includes a drive control unit 55a that controls the curved state of the curved section 52b, an image control unit 55b that controls the imaging unit 58, and a light source control unit 55c that controls a light source device (not illustrated). The control device 55 includes a processor, such as a central processing unit (CPU), and performs overall control of the endoscope system 50. The control device 55 includes the input unit 31, the difference calculating unit 32, the determination unit 33, the buffer 34, and the storage unit 37 that are the components of the control device 3 described above.

The drive control unit 55a includes an actuator and is mechanically connected to the operating unit 53 and the curved section 52b via the wire. The drive control unit 55a controls the curved state of the curved section 52*b* by moving forward and backward the wire. Furthermore, the drive control unit 55*a* includes the drive control unit 35 that is the component of the control device 3 described above, performs feedback control, and moves the movable frame 20 in the optical unit 2 to a desired position.

The image control unit 55*b* is electrically connected to the imaging unit 58 and the operating unit 53 via the electrical wire. The image control unit 55*b* performs drive control of voice coil motors 30A and 30B included in the imaging unit 58 and performs a process on an image captured by the imaging unit 58. The image processed by the image control unit 55*b* is displayed by the display device 57.

The light source control unit 55*c* is optically connected to a light source and the operating unit 53 by the optical fiber. The light source control unit 55*c* controls the brightness of the light source irradiated from the distal end portion 52*a*.

Furthermore, it may also be possible to configure the operating unit 53 such that the operating unit 53 is formed as a separate unit from the insertion portion 52 and performs the operation of the insertion portion 52 by remote control.

Because the endoscope system 50 having the configuration described above includes the imaging unit 58 including the optical unit 2 described above, it is possible to implement a small-sized and high-precision change in zoom or focus operation. Furthermore, because the components of the control device 3 are included, even if abnormality is present in the position signal detected by the position detection unit 100, it is possible to acquire an image maintaining the image quality capable of continuing a treatment given to a subject. Furthermore, if the optical unit 2 is used in the endoscope system 50, the heat resistance resin used for the movable frame 20 or the like is preferably be a resin having a heat resistant temperature of 140° C. or higher.

According to the present disclosure, an advantage is provided in that, while suppressing an increase in size, even in the case where position detection of the moving lens is not normally performed, it is possible to maintain the image quality capable of continuing a treatment given to a subject.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An optical system comprising:
a first optical lens configured to transmit light;
a first movable frame configured to hold the first optical lens, the first movable frame being configured to move along a predetermined direction;
a holding frame configured to hold the first movable frame;
a voice coil motor including a magnet and a coil, the voice coil motor being configured to move the first movable frame relative to the holding frame along the predetermined direction;
a first position detection sensor configured to detect information related to a position of the first movable frame with respect to the holding frame and generate a first position signal; and
a controller comprising hardware, the controller being configured to:
determine, based on the first position signal detected by the first position detection sensor, whether the first position signal is normal;
perform, when the first position signal is determined to be normal, first drive control for driving the first movable frame by controlling, based on the first position signal, a current allowed to flow in the coil or configured to perform, when the first position signal is determined not to be normal, second drive control for driving the first movable frame by flowing a current with a predetermined value in the coil; and
generate a first indication value that indicates a movement position of the first movable frame based on an image signal generated by converting light passing through the first optical lens into an electrical signal,
wherein the controller determines, based on a difference between a signal value of the first position signal and the first indication value, whether the first position signal is normal.

2. The optical system according to claim 1, wherein the controller performs control, as the second drive control, for flowing, in the coil, the current with the predetermined value that causes the first movable frame to move to one of moving ends in a moving range of the first movable frame in the predetermined direction.

3. The optical system according to claim 1, wherein the controller performs control, as the second drive control, for flowing, in the coil, the current that causes the first movable frame to move to a position of focusing, in the optical axis direction of the first optical lens, at a far point or a wide angle.

4. The optical system according to claim 1, further comprising:
a second optical lens configured to transmit light;
a second movable frame configured to hold the second optical lens, the second movable frame being configured to be movable in the predetermined direction independently of the first movable frame; and
a second position detection sensor configured to detect information related to a position of the second movable frame with respect to the holding frame, the second position detection sensor being configured to generate a second position signal, wherein the controller determines whether each of the first position signal and the second position signal is normal, and
the controller performs the first drive control or the second drive control with respect to the first movable frame based on the determination result and performs, when the controller determines that the second position signal is normal, third drive control for driving the second movable frame by controlling, based on the second position signal, the current allowed to flow in the coil or performs, when the controller determines that the second position signal is not normal, fourth drive control for driving the second movable frame by flowing a current with a predetermined value in the coil.

5. The optical system according to claim 4, wherein the controller is configured to receive an input of a first indication signal and of a second indication signal that indicates movement positions of the first movable frame and the second movable frame, respectively, wherein
the controller determines, based on a first difference between a signal value of the first position signal and a signal value of the first indication signal, whether the first position signal is normal and determines, based on a second difference between a signal value of the second position signal and a signal value of the second indication signal, whether the second position signal is normal,
when the controller determines that the first position signal is not normal and the second position signal is normal, the controller changes the signal value of the second indication signal that indicates the movement position of the second movable frame and controls, as the third drive control, based on the changed signal value of the second indication signal and the signal value of the second position signal, the current allowed to flow in the coil, and when the controller determines that the first position signal is normal and the second position signal is not normal, the controller changes the signal value of the first indication signal that indicates the movement position of the first movable frame and controls, as the first drive control, based on the changed signal value of the first indication signal and the signal value of the first position signal, the current allowed to flow in the coil.

6. The optical system according to claim 4, wherein the controller is configured to generate a first indication value and a second indication value that indicate movement positions of the first movable frame and the second movable frame, respectively, based on an image signal generated by converting light passing through the first optical lens and the second optical lens into an electrical signal, wherein the controller determines, based on a first difference between a signal value of the first position signal and the first indication value, whether the first position signal is normal and determines, based on a second difference between a signal value of the second position signal and the second indication value, whether the second position signal is normal, when the controller determines that the first position signal is not normal and the second position signal is normal, the controller changes the second indication value that indicates the movement position of the second movable frame and controls, as the third drive control, based on the changed second indication value and the signal value of the second position signal, the current allowed to flow in the coil, and when the controller determines that the first position signal is normal and the second position signal is not normal, the controller changes the first indication value that indicates the movement position of the first movable frame and the controls, as the first drive control, based on the changed first indication value and the signal value of the first position signal, the current allowed to flow in the coil.

7. The optical system according to claim 1, wherein the first position detection sensor comprises:

a magnetic material disposed on one of the first movable frame and the holding frame, the magnetic material being configured to generate a magnetic field for position detection, and a magnetic sensor disposed on the other one of the first movable frame and the holding frame, the magnetic sensor being configured to detect a magnetic field orthogonal to the movement direction of the first movable frame.

8. An endoscope system configured to be inserted into a subject for observing an interior of the subject, the endoscope system comprising:

an optical system according to claim 1; and an image sensor configured to convert light passing through the first optical lens to an electrical signal.

9. An optical system comprising:

a first optical lens configured to transmit light;

a first movable frame configured to hold the first optical lens, the first movable frame being configured to move along a predetermined direction;

a holding frame configured to hold the first movable frame;

a voice coil motor including a magnet and a coil, the voice coil motor being configured to move the first movable frame relative to the holding frame along the predetermined direction;

a first position detection sensor configured to detect information related to a position of the first movable frame with respect to the holding frame and generate a first position signal; and a controller comprising hardware, the controller being configured to:

determine, based on the first position signal detected by the first position detection sensor, whether the first position signal is normal;

perform, when the first position signal is determined to be normal, first drive control for driving the first movable frame by controlling, based on the first position signal, a current allowed to flow in the coil or configured to perform, when the first position signal is determined not to be normal, second drive control for driving the first movable frame by flowing a current with a predetermined value in the coil; and receive an input of a first indication signal that indicates a movement position of the first movable frame;

wherein the controller determines, based on a difference between a signal value of the first position signal and a signal value of the first indication signal, whether the first position signal is normal; and the controller performs control, as the second drive control, for flowing, in the coil, the current with the predetermined value that causes the first movable frame to move to one of moving ends in a moving range of the first movable frame in the predetermined direction.

10. An optical system comprising:

a first optical lens configured to transmit light;

a first movable frame configured to hold the first optical lens, the first movable frame being configured to move along a predetermined direction;

a holding frame configured to hold the first movable frame;

a voice coil motor including a magnet and a coil, the voice coil motor being configured to move the first movable frame relative to the holding frame along the predetermined direction;

a first position detection sensor configured to detect information related to a position of the first movable frame with respect to the holding frame and generate a first position signal; and a controller comprising hardware, the controller being configured to:

determine, based on the first position signal detected by the first position detection sensor, whether the first position signal is normal;

perform, when the first position signal is determined to be normal, first drive control for driving the first movable frame by controlling, based on the first position signal, a current allowed to flow in the coil or configured to perform, when the first position signal is determined not to be normal, second drive control for driving the first movable frame by flowing a current with a predetermined value in the coil; and receive an input of a first indication signal that indicates a movement position of the first movable frame;

wherein the controller determines, based on a difference between a signal value of the first position signal and a signal value of the first indication signal, whether the first position signal is normal; and the controller performs control, as the second drive control, for flowing, in the coil, the current that causes the first movable frame to move to a position of focusing, in the optical axis direction of the first optical lens, at a far point or a wide angle.

\* \* \* \* \*